(12) United States Patent
Leeflang et al.

(10) Patent No.: US 11,951,262 B2
(45) Date of Patent: *Apr. 9, 2024

(54) CATHETER DEVICES AND METHODS FOR MAKING THEM

(71) Applicant: CLPH, LLC, Palo Alto, CA (US)

(72) Inventors: Stephen A. Leeflang, Sandy, UT (US); Christian S. Eversull, Palo Alto, CA (US)

(73) Assignee: CLPH, LLC, Palo Alto, CA (US)

( * ) Notice: Subject to any disclaimer, the term of this patent is extended or adjusted under 35 U.S.C. 154(b) by 256 days.

This patent is subject to a terminal disclaimer.

(21) Appl. No.: 17/202,164

(22) Filed: Mar. 15, 2021

(65) Prior Publication Data
US 2021/0268228 A1    Sep. 2, 2021

Related U.S. Application Data

(63) Continuation of application No. 16/267,333, filed on Feb. 4, 2019, now Pat. No. 10,946,171, which is a continuation of application No. 15/230,363, filed on Aug. 5, 2016, now Pat. No. 10,195,395, which is a continuation-in-part of application No. PCT/US2015/051284, filed on Sep. 21, 2015.

(60) Provisional application No. 62/250,133, filed on Nov. 3, 2015, provisional application No. 62/201,319, filed on Aug. 5, 2015, provisional application No. 62/053,188, filed on Sep. 21, 2014.

(51) Int. Cl.
*A61M 25/00*    (2006.01)
*A61M 25/01*    (2006.01)

(52) U.S. Cl.
CPC ...... *A61M 25/005* (2013.01); *A61M 25/0012* (2013.01); *A61M 25/0113* (2013.01); *A61M 25/0147* (2013.01)

(58) Field of Classification Search
None
See application file for complete search history.

(56) References Cited

U.S. PATENT DOCUMENTS

| | | | | |
|---|---|---|---|---|
| 5,431,168 | A * | 7/1995 | Webster, Jr. | ....... A61B 18/1492 604/95.04 |
| 10,195,395 | B2 * | 2/2019 | Leeflang | ........... A61M 25/0012 |
| 10,946,171 | B2 * | 3/2021 | Leeflang | ............ A61M 25/005 |
| 2001/0025134 | A1 * | 9/2001 | Bon | .................. A61M 25/0136 600/146 |

(Continued)

*Primary Examiner* — Manuel A Mendez
(74) *Attorney, Agent, or Firm* — William A. English; Vista IP Law Group LLP

(57) ABSTRACT

Catheters, sheaths, or other tubular devices are provided that include a proximal end, a distal end sized for introduction into a patient's body, and a steerable distal portion. The tubular device includes a primary lumen extending between the proximal and distal ends; an auxiliary lumen adjacent the primary lumen; and one or more reinforcement members including windings extending helically along at least the distal portion, at least some of the windings passing between the primary and steering element lumens and at least some of the windings surrounding both the primary and steering element lumens. In one embodiment, a steering element is slidably disposed within the auxiliary lumen. Apparatus and methods for making such tubular devices are also provided.

21 Claims, 18 Drawing Sheets

(56) References Cited

U.S. PATENT DOCUMENTS

2013/0046298 A1\* 2/2013 Kaufman .......... A61M 25/0144
606/1
2014/0323964 A1\* 10/2014 Leeflang .................. D04C 3/48
604/95.04

\* cited by examiner

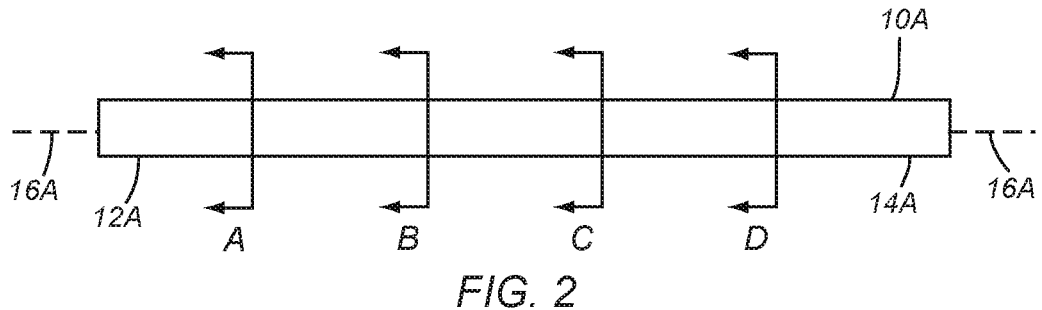
FIG. 2
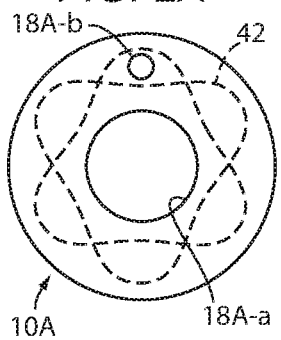 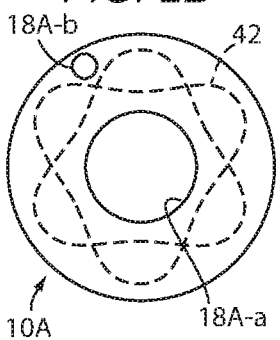 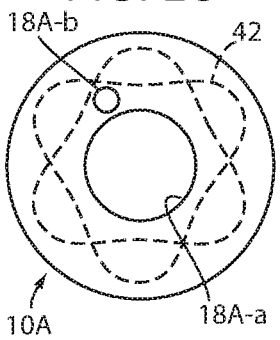 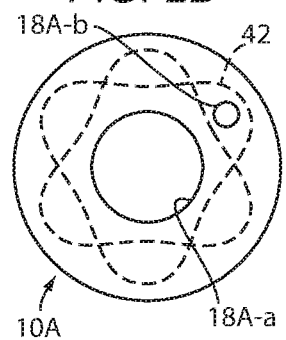
FIG. 2A  FIG. 2B  FIG. 2C  FIG. 2D
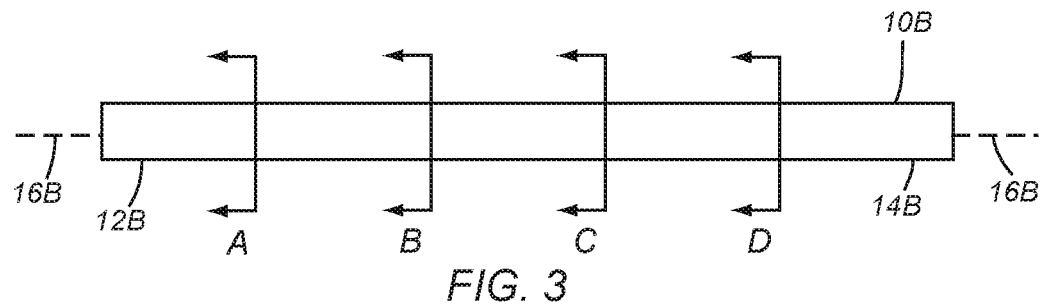
FIG. 3
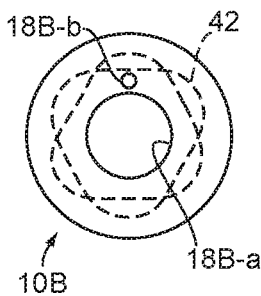 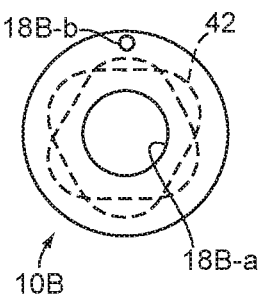 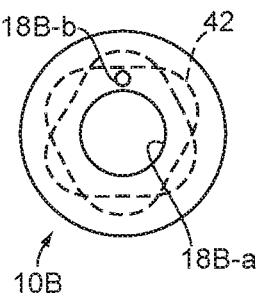 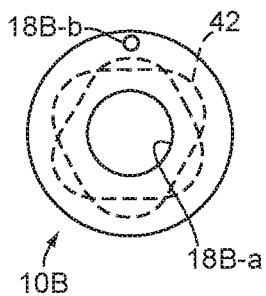
FIG. 3A  FIG. 3B  FIG. 3C  FIG. 3D

LAMINATE
& REMOVE JACKET STOP

REMOVE MANDRELS

RESIDUAL LUMEN WITH OR WITHOUT LINER

ADD PULL WIRE & TRIM BRAID

BRAID TERMINATION

LAMINATE, TRIM, FORM, REMOVE INNER MANDREL

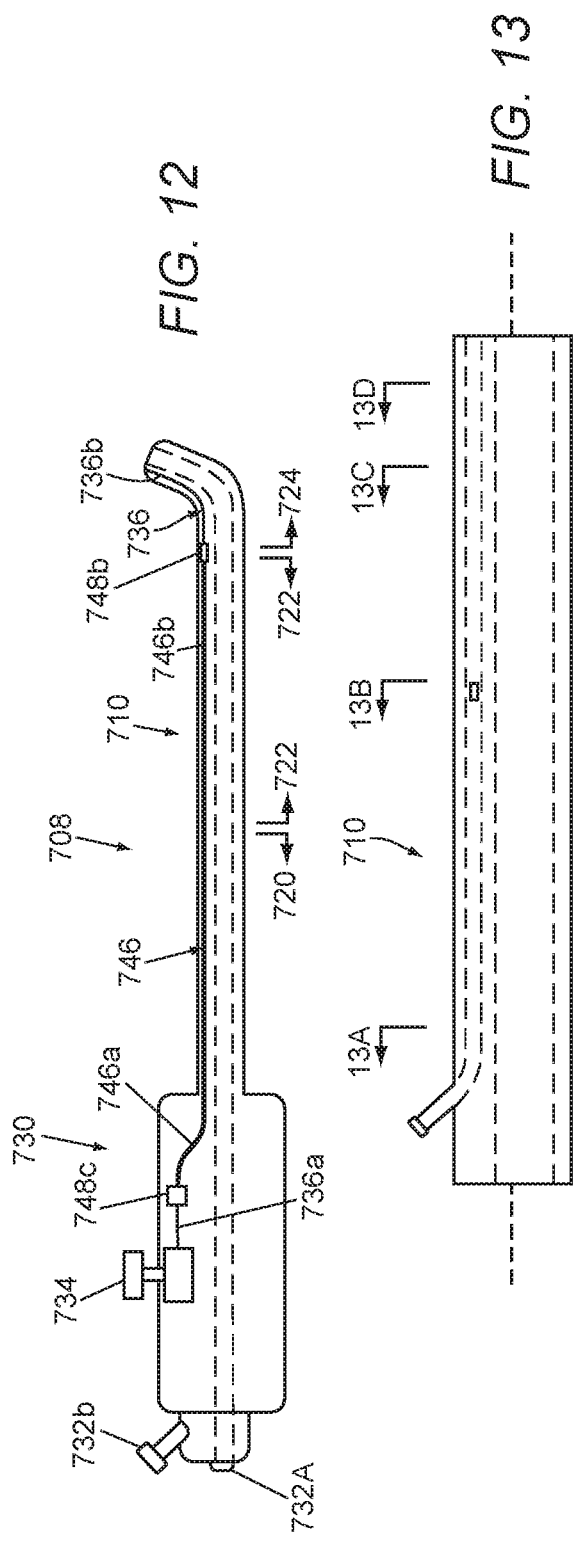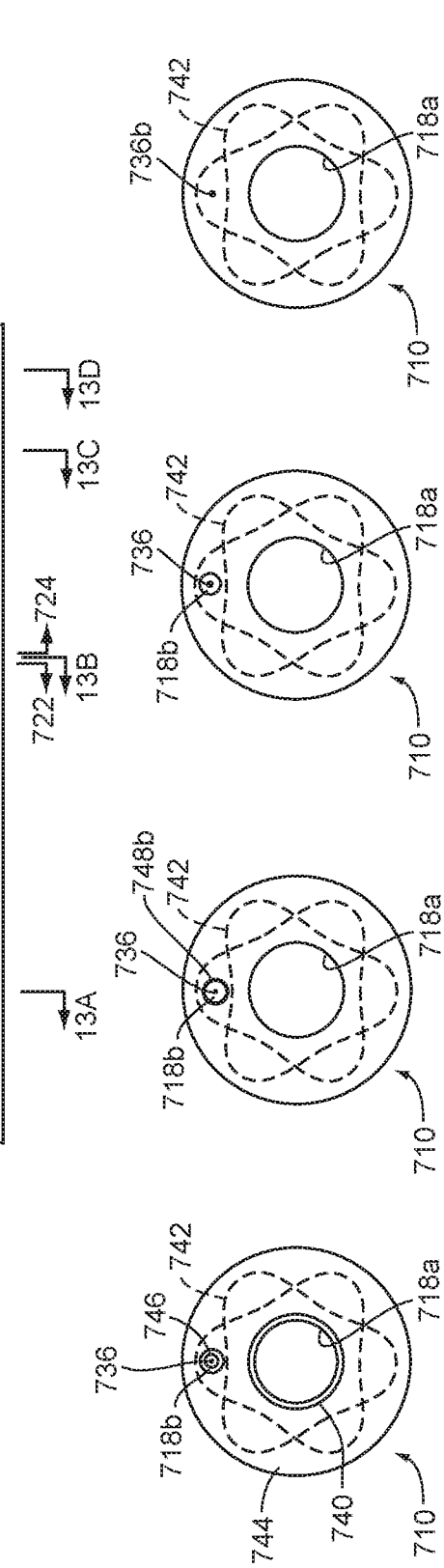

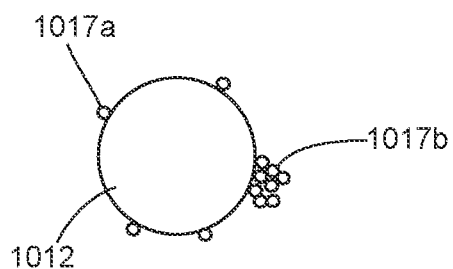
FIG. 20A
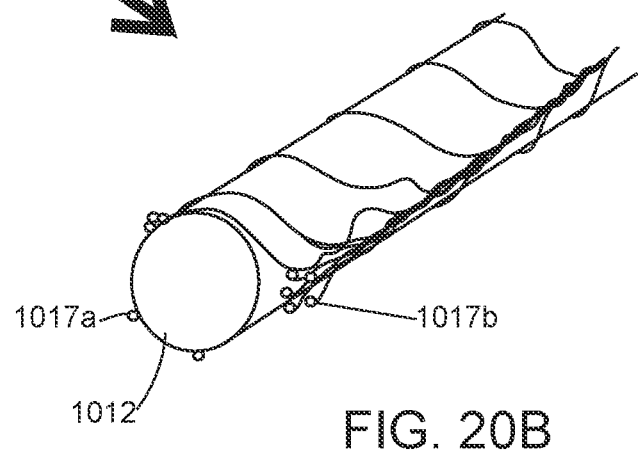
FIG. 20B
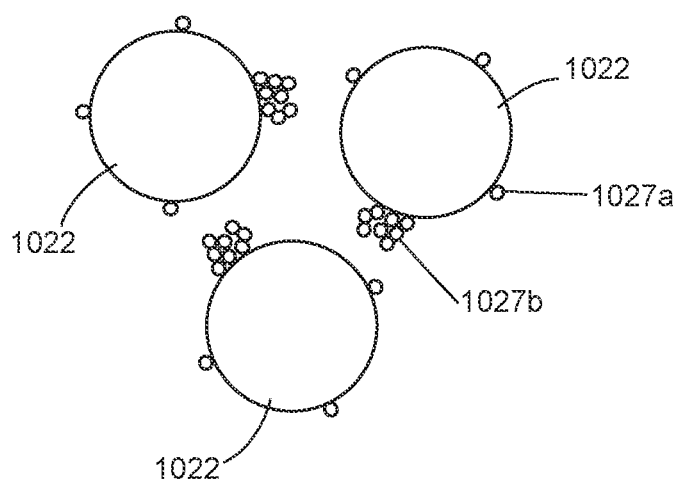
FIG. 21

CATHETER DEVICES AND METHODS FOR MAKING THEM

RELATED APPLICATION DATA

This application is a continuation of application Ser. No. 16/267,333, filed Feb. 4, 2019, and issuing as U.S. Pat. No. 10,946,171, which is a continuation of application Ser. No. 15/230,363, filed Aug. 5, 2016, now U.S. Pat. No. 10,195,395, which claims benefit of provisional application Ser. No. 62/201,319, filed Aug. 5, 2015, and 62/250,133, filed Nov. 3, 2015, and is a continuation-in-part of International application No. PCT/US2015/051284, filed Sep. 21, 2015, which claims benefit of U.S. provisional application Ser. No. 62/053,188, filed Sep. 21, 2014, the entire disclosures of which are expressly incorporated by reference herein.

FIELD OF THE INVENTION

The present invention relates generally to reinforced catheters, sheaths, or other tubular devices including multiple lumens, and, more particularly, to catheters, sheaths, or other tubular devices including braided or other reinforcement configurations and/or including one or more steering elements for deflecting a distal portion of the tubular devices, and to methods for making such tubular devices.

BACKGROUND

Elongate tubular devices, such as diagnostic or treatment catheters or sheaths may be provided for introduction into a patient's body, e.g., the patient's vasculature or other body lumens. For example, a catheter may have a distal portion configured to be introduced into a body lumen and advanced to one or more desired locations within the patient's body by manipulating a proximal end of the catheter.

To facilitate introduction of such a catheter, one or more wires, cables, or other steering elements may be provided within the catheter, e.g., that are coupled to the distal portion and may be pulled or advanced from the proximal end to deflect the distal portion. For example, a steering element may be provided that is intended to deflect the distal portion within a predetermined plane and/or into a desired curved shape.

Pull wires are a common way to impart deflection ability to such a catheter. However, there are a number of drawbacks associated with such pull wires. For example, a pull wire occupies a significant amount of space within the catheter body. In addition, a pull wire frequently needs to be reinforced, e.g., on the inside and outside of the braid or other reinforcement of the catheter, e.g., to prevent "pull through" or loosening when the pull wire is actuated by pushing or pulling, i.e., the resulting bending moment may cause the pull wire to separate layers of or tear at least partially through the wall of catheter, potentially splitting the catheter and/or decreasing the mechanical actuation ability of the pull wire. Further, a pull wire can make the torque properties of the catheter non-homogenous, making it difficult or impossible to torque the catheter when the pull wire is actuated, e.g., within a tortuous pathway. Further, auxiliary lumens, in particular those located in the wall of a large bore sheath, are difficult to manufacture with consistency due to difficulties with alignment, hand assembly, and the like.

Pull and push wire based deflection mechanisms in catheters also create a number of design and performance challenges. These challenges including but are not limited to 1) avoiding undesirable bending/deflection outside of the desired deflection area, 2) avoiding stiffening of the catheter greater than is desirable, 3) avoiding limitation on torque transmission to the distal portion of the device, 4) avoiding high deflection forces, and/or 5) achieving manufacturing flexibility for the position of the deflection segment.

With regards to torque transmission, this challenge depends on at least two important conditions that are present in almost all common catheter uses: 1) the catheter is generally not used in a substantially straight condition (typical paths from entry into the body to the final locations predominantly include moderate to severe tortuosity) and 2) the catheter needs to be able to transmit torque to direct a distal deflectable segment to an ideal location (e.g., deflection alone does not generally provide the navigability desired by the operator).

Torque transmission through even moderate tortuosity becomes a problem when the forces associated with the pull or push wire are asymmetrically loaded onto the cross-section of the catheter. Thus, as the catheter is torqued/rotated around its axis, the path length change that occurs in the cross-section of the catheter from the inside edge of the curve to the outside edge of the curve may interfere with the pull wire. For example, if the pull wire is in tension and is asymmetrically loaded in the periphery of the cross-section and is moving from an area inside the curve to outside the curve, the catheter will need to overcome the force of the pull wire that is "fighting" to stay in a shorter length condition. If the torque properties of the catheter are high and there is residual deflection or compressibility left in the system, the torque may overcome this and rotations can occur.

However, even in this best case scenario, there are two significant limitations. 1) The torque profile as a function of rotation is not constant; in other words, it is unstable and irregular. This problem is commonly known as "whip." 2) The change in path length of the pull wire may cause the pull wire to pull more/harder and may cause the deflection or actuation amplitude to increase. Alternatively, catheters without sufficient torque characteristics remain "stuck" in a narrow band of rotation and are unable to overcome the "whip." Continued rotation/torque of the devices may instead cause a torsional kink in the device rather than rotation of the distal tip.

With regards to undesirable deflection, in addition to being unsightly, the undesired deflection that occurs through simple eccentrically-located push/pull systems may be problematic in many clinical situations, primarily those in which the catheter is operating in an open space, such as those of the heart or large vessels. Although variations in stiffness may shift the balance of deflection to a specific area, even a very stiff catheter (as stiff as is known in the art) may still list to one side in a segment outside the specified deflection segment depending on whether push or pull of the activation element is being used. This causes, for example, the non-primary deflection section of the catheter (usually close behind the deflectable segment) to list to the side. This may significantly reduce the level of control that the operator has as each action causes a separate reaction the results of which sometimes mean the operator cannot find a suitable solution.

Similarly, simple eccentrically-located push/pull systems may require the non-deflection sections to be substantially stiffer. This may cause a number of problems including but not limited to 1) ability to track through the anatomy, 2) damage to the anatomy, 3) and/or adverse effect on positioning within a lumen or chamber.

Additionally, deflection forces are not just a function of catheter stiffness and friction; they are also a function of the lever arm radius. The position of these push/pull actuators is currently limited by the need to have the pull wire inside the braid (the deflection forces pull outward against the braid—otherwise the pull/push element is likely to break through the outer surface of the catheter.

Yet other problems may exist, which may be appreciated by those skilled in the art, including loss of sensitivity due to changes in the shaft (or, e.g., changes in the length of the shaft due to heat, humidity, compression or extension forces, etc.).

Accordingly, there is a need for improved catheters, sheaths, and other tubular devices and methods of their manufacture.

SUMMARY

The present invention is directed to reinforced catheters, sheaths, or other tubular devices including multiple lumens. More particularly, the present invention is directed to catheters, sheaths, or other tubular devices, e.g., steerable tubular devices, including braided or other reinforcement configurations and/or including one or more steering elements for deflecting a distal portion, and/or to methods for making such catheters, sheaths, or other tubular devices. In exemplary embodiments, the tubular devices may include one or more lumens that change position relative to the reinforcement members and/or a central lumen along the length of the tubular devices. In addition or alternatively, the systems and methods herein may allow one or more lumens to be created that extend only partially along the length of the tubular devices, e.g., from a distal tip to a side port outlet offset proximally from the distal tip (e.g., similar to a rapid-exchange lumen), from a proximal end to a side port at an intermediate or distal location, and the like.

In accordance with one embodiment, a tubular device is provided, e.g., for a catheter or sheath, comprising a proximal end and a distal end sized for introduction into a patient's body. The tubular device may include a central lumen extending between the proximal and distal ends; an auxiliary lumen extending between the proximal and distal ends adjacent the central lumen; and one or more reinforcement members including windings extending around the central lumen between the proximal and distal ends. In addition, one or more layers may surround the one or more reinforcement members and/or the lumens. At one or more locations along the length of the tubular device, the auxiliary lumen may change position relative to the reinforcement members, e.g., may be at least partially braided, woven, or directed into the reinforcement members, between the reinforcement members and the central lumen, and outside the reinforcement members along different portions of the tubular device.

In accordance with yet another embodiment, a method is provided for making a tubular body that includes directing a primary mandrel along a central axis of a braiding apparatus such that the primary mandrel is surrounded by a plurality of horn gears and/or bobbin carriers or other reinforcement carrying elements; and directing a secondary mandrel adjacent to the primary mandrel and offset from the central axis. One or more reinforcement members from the reinforcement carrying elements may be wrapped around the primary mandrel, and an outer jacket may be applied around the primary and secondary mandrels after wrapping the one or more reinforcement members.

Along a first portion of the primary mandrel, the reinforcement members may be directed such that some windings of the reinforcement members surround the primary mandrel and pass between the primary mandrel and the secondary mandrel, and some windings of the reinforcement members surround both the primary and secondary mandrels. Along a second portion of the primary mandrel, all of the windings of the reinforcement members may surround both the primary mandrel and the secondary mandrel. Optionally, along a third portion of the primary mandrel, the reinforcement members may be wrapped around the primary mandrel such that the secondary mandrel is outside the reinforcement members. It will be appreciated that the locations of these portions may be exchanged to desired locations along the length of the tubular devices, as desired. In addition or alternatively, optionally along additional one or more sections, the secondary mandrel(s) may terminate or originate at any point along the one or more additional sections.

Alternatively, along a first portion of the primary mandrel, all of the windings of the reinforcement members may surround both the primary mandrel and the secondary mandrel, and along a second portion, the reinforcement members may be directed such that some windings of the reinforcement members surround the primary mandrel and pass between the primary mandrel and the secondary mandrel, and some windings of the reinforcement members surround both the primary and secondary mandrels. Optionally, along a third portion of the primary mandrel, the reinforcement members may be wrapped around the primary mandrel such that the secondary mandrel is outside the reinforcement members.

In another alternative, along a first portion of the primary mandrel, the reinforcement members may be wrapped around the primary mandrel such that the secondary mandrel is outside the reinforcement members, and along a second portion of the primary mandrel, all of the windings of the reinforcement members may surround both the primary mandrel and the secondary mandrel or the reinforcement members may be wrapped around the primary mandrel such that the secondary mandrel is outside the reinforcement members The primary mandrel may be removed to define a primary lumen within the tubular body. In addition, the method may also include removing the secondary mandrel to define an auxiliary lumen within the tubular body adjacent the primary lumen. As a result, the position of the auxiliary lumen, e.g., radially and/or circumferentially relative to the primary lumen, may change and/or begin or end at desired locations along the length of the tubular body, e.g., between the first, second, and/or optionally third portions.

In accordance with another embodiment, a method is provided for making a tubular body that includes directing a primary mandrel along a central axis of a braiding apparatus such that the primary mandrel is surrounded by a plurality of reinforcement carrying elements; providing a plurality of reinforcement carrying elements in a predetermined configuration relative to the central axis; providing a source of a secondary mandrel at a first location adjacent to the primary mandrel and offset from the central axis; with the secondary mandrel feeding from the source at the first location, wrapping reinforcement members from the reinforcement carrying elements helically around a first portion of the primary mandrel such that some windings of the one or more reinforcement members surround the primary mandrel and pass between the primary mandrel and the secondary mandrel and some windings of the one or more reinforcement members surround both the primary and secondary mandrels; moving the source of secondary mandrel to a second location; with the secondary mandrel feeding from the source at the second location, wrapping reinforcement members from the reinforcement carrying elements helically around a second portion of the primary mandrel such that either a) all of the reinforcement members also surround the secondary mandrel; or b) the second secondary mandrel remains outside the reinforcement members. An outer jacket (which may have a uniform construction or a variable construction along different regions) may be applied around the primary and secondary mandrels after wrapping the one or more reinforcement members therearound; and the primary mandrel may be removed to define a primary lumen within the tubular body.

In accordance with still another embodiment, a method is provided for making a tubular body using a braiding apparatus comprising a primary mandrel source configured to direct a primary mandrel along a central axis, a plurality of horn gears rotatably mounted around the central axis in a predetermined arrangement such that the horn gears rotate about respective horn gear axes and carriers travel along a generally circular path around the central axis during operation of the braiding apparatus, and a secondary mandrel source configured to direct a secondary mandrel towards the primary mandrel from one of a plurality of locations comprising a first location disposed adjacent the central axis within the generally circular path, a second location aligned with a horn axis of one of the horn gears, and a third location outside the generally circular path. The method may include braiding a first portion of the primary mandrel by: a) directing the primary mandrel along the central axis; b) directing the secondary mandrel from one of the plurality of locations towards the primary mandrel such that the secondary mandrel is disposed adjacent the first portion of the mandrel; and c) wrapping reinforcement members from the carriers around the first portion of the primary mandrel. The method may also include braiding a second portion of the primary mandrel by: a) moving the secondary mandrel source another of the plurality of locations; b) directing the primary mandrel further along the central axis; and c) wrapping reinforcement members from the carriers around the second portion of the primary mandrel. An outer jacket may be applied around the first and second portions of the primary mandrel and the secondary mandrel, and the primary mandrel may be removed to define a primary lumen within the tubular body. Optionally, the secondary mandrel may be removed or may remain within the tubular body.

In accordance with yet another embodiment, a tubular device is provided for a catheter or sheath comprising a proximal end and a distal end sized for introduction into a patient's body that includes a central lumen extending between the proximal and distal ends; an auxiliary lumen extending at least partially between the proximal and distal ends adjacent the central lumen; one or more reinforcement members comprising windings extending helically around the central lumen between the proximal and distal ends; and one or more layers surrounding the one or more reinforcement members, wherein the tubular device comprises a first portion in which at least some of the windings pass between the central and auxiliary lumens and at least some of the windings surround both the central and auxiliary lumens, and a second portion in which either a) all of the windings surround both the central and auxiliary lumens or b) all of the windings surround the central lumen and the auxiliary lumen is disposed outside the windings.

In accordance with still another embodiment, an apparatus is provided for performing a procedure within a patient's body that includes a tubular member comprising a proximal end, a distal end sized for introduction into a patient's body, a central axis extending therebetween, and a distal portion extending distally from an intermediate portion to the distal end; a primary lumen extending between the proximal and distal ends and surrounding at least a portion of the central axis; a steering element lumen extending at least partially between the proximal and distal ends adjacent the primary lumen; a steering element(s) slidably disposed within the steering element lumen(s) and comprising a distal end fixed to the tubular member distal end and a proximal end adjacent the proximal end of the tubular member; and an actuator on the proximal end coupled to the steering element proximal end such that, actuation of the actuator applies axial tension or compression to the steering element, thereby causing the distal portion to bend. One or more reinforcement members comprising windings may extend around the primary lumen between the proximal and distal ends, and one or more layers may surround the one or more reinforcement members, wherein the tubular member comprises a first portion in which at least some of the windings pass between the primary lumen and the steering element lumen and at least some of the windings surrounding both the primary lumen and the steering element lumen, and a second portion in which either a) all of the windings surround both the primary lumen and the steering element lumen or b) all of the windings surround the primary lumen and the steering element lumen is disposed outside the windings.

In accordance with another embodiment, an apparatus is provided for performing a procedure within a patient's body that includes a tubular member comprising a proximal end, a distal end sized for introduction into a patient's body, a central axis extending therebetween, and a distal portion extending distally from an intermediate portion to the distal end; a primary lumen extending between the proximal and distal ends and surrounding at least a portion of the central axis; a steering element lumen extending at least partially between the proximal and distal ends adjacent the primary lumen; a steering element slidably disposed within the steering element lumen and comprising a distal end fixed to the tubular member distal end and a proximal end adjacent the proximal end of the tubular member; an actuator on the proximal end coupled to the steering element proximal end such that, actuation of the actuator applies axial tension or compression to the steering element, thereby causing the distal portion to bend; and a compression-resistant element slidably disposed within the steering element lumen and extending from the proximal end through the intermediate portion adjacent the steering element for preventing forces from the steering element from transferring to the tubular member proximal to the distal portion.

In accordance with still another embodiment, a tubular device is provided for a catheter or sheath comprising a proximal end and a distal end sized for introduction into a patient's body, the tubular device including a lumen extending at least partially between the proximal and distal ends; a plurality of reinforcement members comprising windings extending helically around the lumen at least partially between the proximal and distal ends; and one or more layers surrounding the one or more reinforcement members, wherein the reinforcement members have a braiding configuration where at least one of a density and a pitch angle of the reinforcement members vary around a periphery of the lumen. For example, the braiding configuration may include a relatively low density of strands of the reinforcement members around a first region of the periphery of the lumen and a relatively high density of strands of the reinforcement members a second region of the periphery and/or the strands around the first region may define a first pitch angle and the strands around the second region define a second pitch angle that is lower than the first pitch angle.

In accordance with yet another embodiment, a tubular device is provided for a catheter or sheath comprising a proximal end and a distal end sized for introduction into a patient's body, the tubular device including a plurality of lumens extending at least partially between the proximal and distal ends; a plurality of reinforcement members comprising windings extending helically around the lumens at least partially between the proximal and distal ends; and one or more layers surrounding the one or more reinforcement members, wherein the reinforcement members have a braiding configuration where at least one of a density and a pitch angle of the reinforcement members vary around peripheries of the lumens.

In accordance with another embodiment, a method is provided for making a tubular body using a braiding apparatus comprising a plurality of horn gears rotatably mounted around a central axis in a predetermined arrangement such that the horn gears rotate about respective horn gear axes and carriers travel along a generally circular path around the central axis during operation of the braiding apparatus. The method may include directing an elongate first mandrel through a first passage aligned with a first horn gear axis of a first horn gear of the horn gears towards the central axis; wrapping reinforcement members from the carriers around the first mandrel to create a braided assembly having a braiding configuration where at least one of a density and a pitch angle of the reinforcement members vary around a periphery of the first mandrel; and applying an outer jacket around the braided assembly to provide a tubular body. For example, the braiding configuration may include a relatively low density of strands of the reinforcement members around a first region of the periphery of the first mandrel and a relatively high density of strands of the reinforcement members a second region of the periphery and/or the strands around the first region may define a first pitch angle and the strands around the second region define a second pitch angle that is lower than the first pitch angle.

In accordance with still another embodiment, a method is provided for making a tubular body using a braiding apparatus comprising a plurality of horn gears rotatably mounted around a central axis in a predetermined arrangement such that the horn gears rotate about respective horn gear axes and carriers travel along a generally circular path around the central axis during operation of the braiding apparatus. For example, the method may include directing a plurality of elongate mandrels through passages aligned with horn gear axes of respective horn gears of the horn gears towards the central axis; wrapping reinforcement members from the carriers around the mandrels to create a braided assembly having a braiding configuration where at least one of a density and a pitch angle of the reinforcement members vary around a periphery of the mandrels; applying an outer jacket around the braided assembly to provide a tubular body; and removing the mandrels to define respective lumens within the tubular body.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which:

FIG. 2 is a side view of a first example of a catheter including a primary lumen and an auxiliary lumen that changes position along the length of the catheter.

FIGS. 2A-2D are cross-sectional views of the catheter of FIG. 2 taken at different locations along the length of the catheter.

FIG. 3 is a side view of a second example of a catheter including a primary lumen and an auxiliary lumen that changes position along the length of the catheter.

FIGS. 3A-3D are cross-sectional views of the catheter of FIG. 2 taken at different locations along the length of the catheter.

FIG. 12 is a cross-sectional side view of a steerable catheter including a compression-resistant coil surrounding a steering element.

FIG. 13 is a side view of an exemplary embodiment of a tubular body that may be provided for the catheter of FIG. 12.

FIGS. 13A-13D are cross-sectional views of the tubular body of FIG. 13 taken along sections 13A-13A, 13B-13B, 13C-13C, and 13D-13D, respectively.

FIGS. 20A and 20B are cross-sectional and perspective views, respectively, of a braiding configuration of reinforcement elements braided around a single primary mandrel.

FIG. 21 is a cross-sectional view showing an exemplary braiding configuration of reinforcement elements braided around three primary mandrels.

FIGS. 22A and 22B are cross-sectional views showing alternative braiding configurations that may be provided depending on which horn gears the primary mandrels are fed through.

DETAILED DESCRIPTION OF THE EXEMPLARY EMBODIMENTS

Figure 1A:
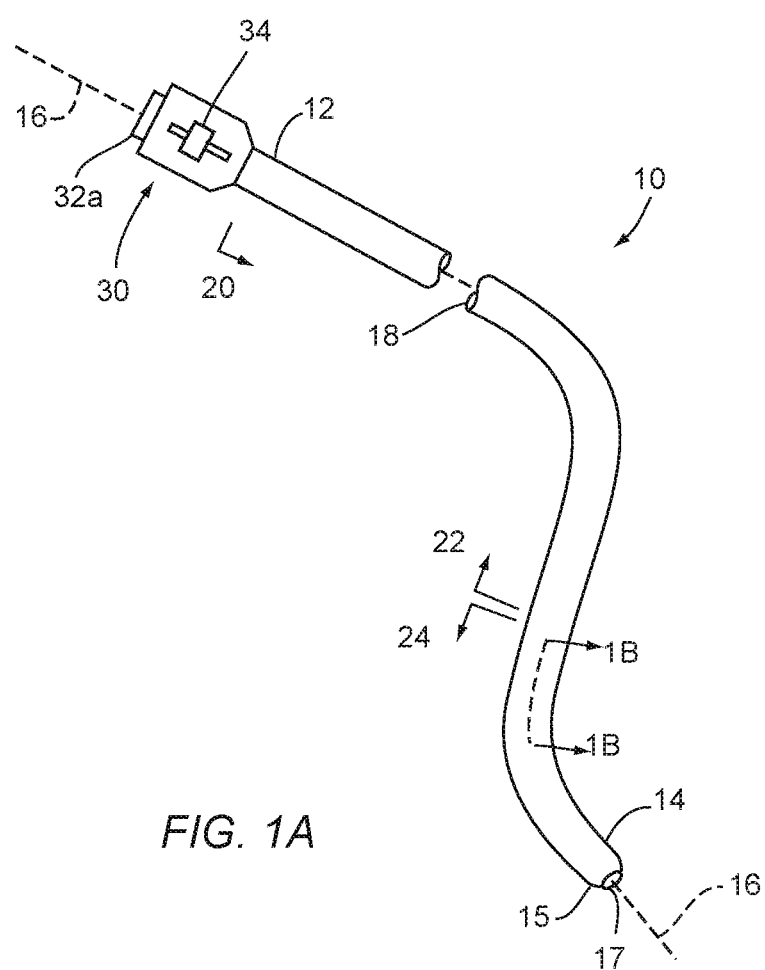
FIG. 1A is a perspective view of an exemplary embodiment of a catheter, including multiple lumens extending between proximal and distal ends thereof, and including a steerable distal portion.
Figure 1B:
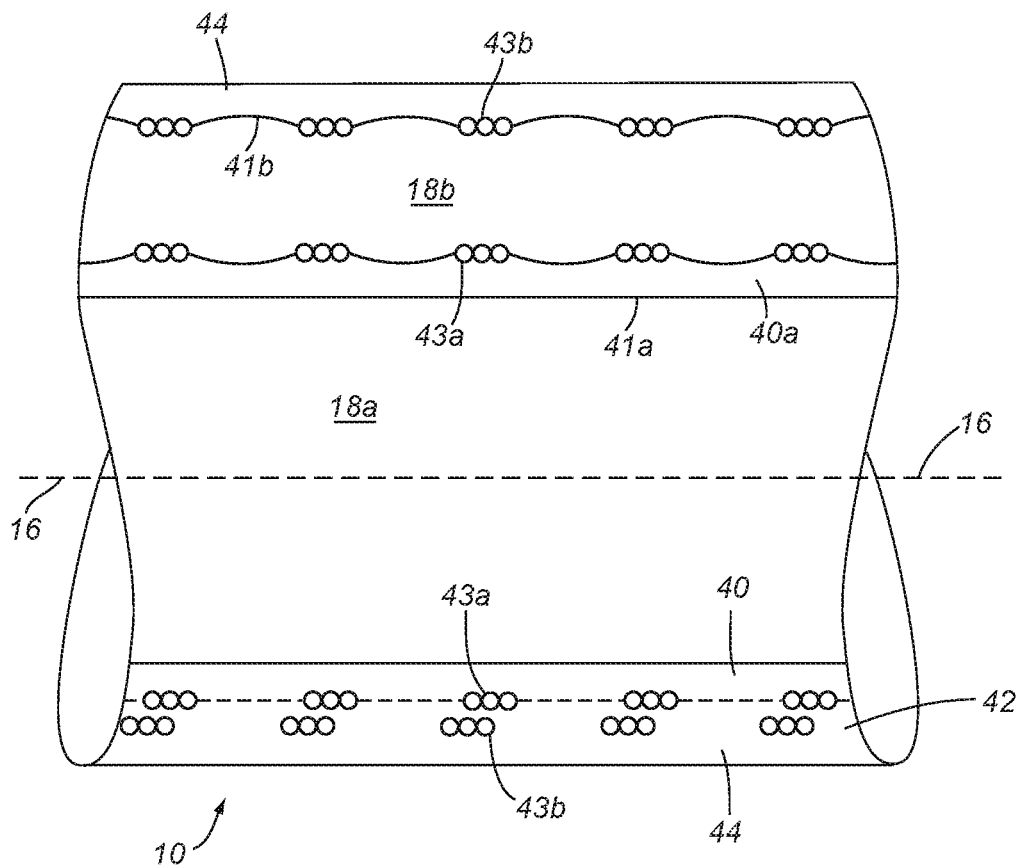
FIG. 1B is a cross-sectional side view of the catheter of FIG. 1A, taken along line 1B-1B, showing reinforcement members positioned around primary and auxiliary lumens of the catheter.

Turning to the drawings, FIGS. 1A and 1B show an exemplary embodiment of an apparatus 10 for introduction into a body lumen (not shown), e.g., for performing a diagnostic and/or therapeutic procedure within a patient's body. In exemplary embodiments, the apparatus 10 may be a guide catheter, a sheath, a procedure catheter, e.g., an imaging catheter, an ablation and/or mapping catheter, a balloon catheter, or other tubular device sized for introduction into a body lumen, such as a vessel within a patient's vasculature, a passage within a patient's gastrointestinal tract, urogenital tract, reproductive tract, respiratory tract, lymphatic system, and the like (not shown). In exemplary embodiments, the apparatus 10 may have a length between about ten and one hundred thirty centimeters (10-130 cm), and an outer diameter between about four and twenty-four French (4-24 Fr or 1.33-8.0 mm).

Generally, the apparatus 10 is an elongate tubular member including a proximal end 12, a distal end 14 sized for insertion into a body lumen, a central longitudinal axis 16 extending between the proximal and distal ends 12, 14, and one or more lumens 18 extending between the proximal and distal ends 12, 14. For example, as shown in FIG. 1B, the apparatus 10 may include a central or primary lumen 18a, e.g., sized for receiving or carrying one or more instruments or other elements (not shown). In exemplary embodiments, the central lumen 18a may be sized for receiving or carrying a guide wire, procedure catheter, balloon catheter, ablation catheter, cardiac lead, needle, or other instrument (not shown), one or more wires or other conductors, one or more optical fibers, one or more tubes or accessory lumens, one or more mechanical elements, one or more sensors, and/or sized for delivering and/or removing fluids or other flowable agents or materials therethrough.

In one embodiment, shown in FIG. 1A, the central lumen 18a may exit at or communicate with an outlet 17 in the distal end 14, e.g., to allow a guidewire or other instrument (not shown) to pass therethrough and/or for delivering or aspirating fluid therethrough. Alternatively, the central lumen 18a may be enclosed, e.g., terminating within or adjacent the distal end, e.g., by an electrode, cap, or other component (not shown) to isolate the central lumen 18a and/or elements carried therein from the environment outside the apparatus 10.

Returning to FIG. 1B, in addition to the central lumen 18a, the apparatus 10 includes an auxiliary lumen 18b, e.g., extending adjacent the central lumen 18a, e.g., substantially parallel to and radially offset relative to the central axis 16. For example, in FIG. 5, an exemplary embodiment of a catheter 110 is shown in which the auxiliary lumen 118b may be a steering element lumen configured to receive a pull wire or other steering element 136 therein, e.g., to bend or otherwise deflect a distal portion of the catheter 110, as described further below. In FIG. 6, an exemplary embodiment of a catheter 210 is shown in which the auxiliary lumen 218b may receive one or more wires or conductors 236 for coupling to one or more electrodes 238 mounted on the distal portion of the catheter 210, also as described further below.

With continued reference to FIGS. 1A and 1B, optionally, the apparatus 10 may include one or more additional lumens (not shown), e.g., one or more additional steering element lumens, conductor lumens, inflation lumens (e.g., if the apparatus 10 includes one or more balloons, not shown on the distal end 14), and/or accessory lumens. For example, a pair of auxiliary lumens may be provided (not shown) on opposite sides of the apparatus 10, e.g., offset about one hundred eight degrees (180°) around the circumference of the apparatus 10.

Optionally, the auxiliary lumen(s) may have a variety of cross-sectional shapes and/or sizes, e.g., a substantially circular shape, an elliptical or oval shape, a substantially rectangular shape, a triangular shape, a pair of overlapping circles shape, and the like, e.g., similar to the devices disclosed in U.S. Publication No. 2014/0323964, the entire disclosure of which is expressly incorporated by reference herein. The shape and/or size of the auxiliary lumen(s) may be substantially uniform along the length of the apparatus 10 or may vary at different locations, as described elsewhere herein.

The auxiliary lumen 18b is generally radially offset from the central axis 16 substantially along the length of the apparatus 10, e.g., entirely from the distal end 14 to the proximal end 12. In addition, the radial and/or circumferential position of the auxiliary lumen 18b may change relative to the primary lumen 18a and/or other components of the apparatus 10 at various locations along the length of the apparatus 10, as described elsewhere herein.

Returning to FIG. 1A, the distal end 14 may include a tapered, rounded, or otherwise shaped distal tip 15, e.g., to provide a substantially atraumatic tip and/or to facilitate advancement or navigation through various anatomy. In addition or alternatively, the distal end 14 may include one or more therapeutic and/or diagnostic elements, e.g., one or more balloons, stents, sensors, electrodes, ablation elements, thermocouples, steering mechanisms, imaging devices, helical anchors, needles, and the like (not shown), depending upon the particular intended application for the apparatus 10. Further, in addition or alternatively, the distal end 14 may include one or more markers or other features to enhance radiopacity and/or visibility under ultrasound, Mill or other imaging modalities, e.g., by mounting one or more platinum elements on the distal end 14, doping one or more regions of the distal end 14 with tungsten or barium sulfate, and/or other methods known in the art.

Optionally, as shown in FIG. 1A, the proximal end 12 may include a handle or hub 30, e.g., configured and/or sized for holding and/or manipulating the apparatus 10 from the proximal end 12. In addition, the handle 30 may include one or more ports, e.g., port 32a communicating with the central lumen 18a, or other respective lumens (not shown). Optionally, the port 32a may include one or more valves, e.g., a hemostatic valve (also not shown), which may provide a substantially fluid-tight seal, while accommodating insertion of one or more instruments or fluids into the central lumen 18a. Optionally, a side port (not shown) may be provided on the handle 30, e.g., for delivering fluid into and/or aspirating fluid from the primary lumen 18a, e.g., around an instrument inserted into the primary lumen 18a. Optionally, the handle 30 and/or proximal end 12 may include one or more connectors, such as luer lock connectors, electrical connectors or cables, and the like, for connecting other devices (not shown) to the apparatus 10, such as syringes, displays, controllers, and the like (also not shown).

In addition, the handle 30 may include one or more actuators, such as sliders, buttons, switches, rotational actuators, and the like, e.g., for activating and/or manipulating components (also not shown) on the distal end 14 or otherwise operating the apparatus 10. For example, as shown in FIG. 1A, an actuator 34 may be provided that is coupled to a proximal end of a steering element (not shown) within the auxiliary lumen 18b, e.g., similar to the embodiment shown in FIG. 5, as described further elsewhere herein.

Generally, with particular reference to FIG. 1B, the apparatus 10 may include an inner liner 40, e.g., at least partially or entirely surrounding or otherwise defining the central lumen 18a, a reinforcement layer 42 surrounding the inner liner 40, and an outer jacket 44 surrounding and/or encasing the reinforcement layer 42, each of which may extend at least partially between the proximal and distal ends 12, 14 of the apparatus 10. The reinforcement layer 42 and/or outer jacket 44 may be attached to the inner liner 40, e.g., by laminating, adhering, adhesive bonding, ultrasonic welding, reflowing or other heating, and the like, as described elsewhere herein.

In an exemplary embodiment, the central lumen 18a is defined by an inner liner 40a including an inner surface 41a. The inner liner 40a may be formed from lubricious material, e.g., PTFE, to provide a lubricious inner surface 41a. Alternatively, the inner liner 40 may be formed from one or more layers of thermoplastic or other polymeric material including one or more coatings on the inner surface 41a having desired properties, e.g., a hydrophilic and/or lubricious coating, e.g., similar to the liners disclosed in U.S. Pat. Nos. 7,550,053 and 7,553,387, and U.S. Publication No. 2009/0126862, the disclosures of which are expressly incorporated by reference herein.

Optionally, as shown in FIG. 1B, an inner liner 40b may also at least partially surround the auxiliary lumen 18b, which may be formed from a lubricious material and/or may include one or more coatings on its inner surface 41b, similar to the inner liner 40a. The inner surface 41b of the auxiliary lumen 18b may have a substantially uniform cross-section, as shown in FIG. 1B. Alternatively, the inner surface 41b of the auxiliary lumen 18b may have a textured or other variable cross-section along, e.g., along its length and/or about its circumference (not shown).

Optionally, any or all of the inner liner 40a, reinforcement layer 42, and/or outer jacket 44 may be formed from multiple layers of like or different materials (not shown), e.g., to provide desired material properties in the different portions of the apparatus 10. In an exemplary embodiment, the outer jacket 44 may be formed from PEBAX, nylon, urethane, and/or other thermoplastic material, e.g., such that the material of the outer jacket 44 may be heated and reflowed and/or otherwise formed around the components defining the lumens 18, e.g., as described elsewhere herein.

In one embodiment, one or more of the layers of the apparatus 10 may have a substantially homogenous construction between the proximal and distal ends 12, 14. Alternatively, the construction may vary along the length of the apparatus 10 to provide desired properties, e.g., between proximal, intermediate, and distal portions 20, 22, 24. For example, a proximal portion 20 of the apparatus 10 adjacent the proximal end 12 may be substantially rigid or semi-rigid, e.g., providing sufficient column strength to allow the distal end 14 of the apparatus 10 to be pushed or otherwise manipulated from the proximal end 12, while the distal portion 24 may be substantially flexible. As described further below, the distal portion 24 of the apparatus 10 may be steerable, i.e., may be bent, curved, or otherwise deflected substantially within a steering plane, as described further below.

Figure 4A:
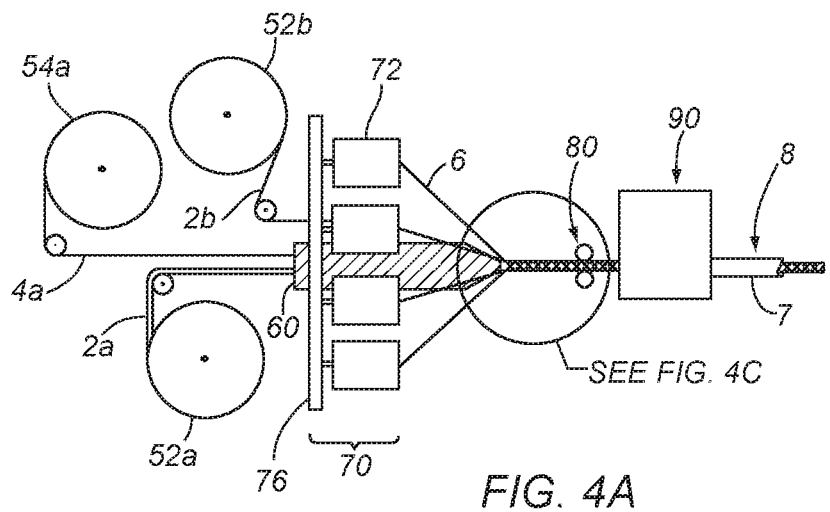
FIG. 4A is a schematic of an exemplary embodiment of a braiding apparatus for making a reinforced tubular member including multiple mandrels supported by reinforcement members.
Figure 4B:
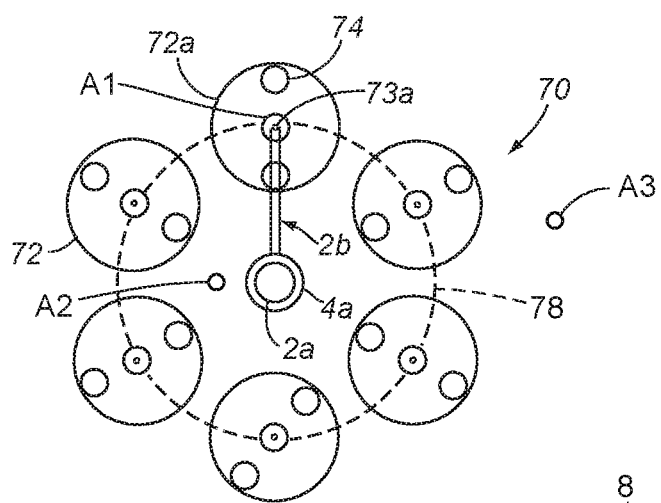
FIG. 4B is a front view of an arrangement of horn gears for creating a braided configuration of reinforcement members that may be included in the braiding apparatus of FIG. 4A and including various locations for sources of mandrels.

Returning to FIG. 1B, the reinforcement layer 42 may include one or more reinforcing members, e.g., wound in a braided or other helical configuration around the inner liner 40a, e.g., using a braiding apparatus such as that shown in FIGS. 4A and 4B, and the outer jacket 44 may include one or more tubular layers surrounding the reinforcement layer 42 and/or between the reinforcement layer 42 and the inner liner 40a. In an exemplary embodiment, the reinforcement layer 42 may include one or more, or a plurality of, round or flat (e.g., rectangular, elliptical, or flat oval) wires, filaments, strands, or other reinforcement members 43, e.g., formed from metal, such as stainless steel, plastic, such as PEEK, glass, woven or twisted fibers, such as aramid, and the like, or composite materials.

In one embodiment, a plurality of reinforcement members 43 may be braided around the inner liner 40a, e.g., with each reinforcement member 43 having the same material and/or shape. Alternatively, the reinforcement members 43 may have different sizes, materials, and/or shapes, e.g., a first size or shape extending helically in a first direction and a second size or shape (different than the first) extending helically in a second direction (e.g., opposite the first direction).

The reinforcement layer 42 may be configured to substantially transfer torsional forces between the proximal and distal ends 12, 14, e.g., to allow the apparatus 10 to be twisted from the proximal end 12 to rotate the distal end 14 about the longitudinal axis 16 within a patient's body. In addition, the reinforcement layer 42 may allow the distal end 14 of the apparatus 10 to be advanced or otherwise manipulated within a patient's body from the proximal end 12 without substantial risk of buckling and/or kinking. Optionally, the pitch of the reinforcement layer 42 may be varied along the length of the apparatus 10, e.g., in order to optimize mechanical properties of various segments or portions of the apparatus 10, e.g., as described elsewhere herein.

In addition, the location of the reinforcement layer 42 may vary relative to the central lumen 18a and/or auxiliary lumen 18b, e.g., as the auxiliary lumen 18b transitions to different radial locations within the wall of the apparatus 10. For example, FIG. 2 shows an example of a catheter 10A that includes a central lumen 18A-a that extends substantially along a central axis 16A and is surrounded by a reinforcement layer 42, which may be similar to any of the embodiments described elsewhere herein. In addition, the catheter 10A includes an auxiliary lumen 18A-b that extends between proximal and distal ends 12A, 14A of the catheter 10A adjacent the central lumen 18A-a at different radial and/or circumferential locations. As shown in FIG. 2A, along a proximal portion, the auxiliary lumen 18A-b may be braided into the reinforcement layer 42, while, as shown in FIG. 2B, at an intermediate portion, the auxiliary lumen 18A-b may transition outside the reinforcement layer 42. Further, as shown in FIG. 2C, the auxiliary lumen 18A-b may transition to a location closer to the central lumen 18A-a such that the reinforcement layer 42 surrounds both lumens 18A-a, 18A-b. Finally, as shown in FIG. 2D, the auxiliary lumen 18A-b may transition again and be braided into the reinforcement layer 42 along a distal portion to the distal end 14A.

With continued reference to FIGS. 2 and 2A-D, in an exemplary embodiment, a deflectable catheter shaft may be constructed wherein one or more auxiliary lumens 18A-b (e.g., a single auxiliary lumen or two auxiliary lumens spaced approximately one hundred eighty degrees (180°) apart) may be braided into or within the reinforcement layer 42 as shown in FIG. 2D at an intermediate portion (e.g., corresponding to FIG. 2 sections B and/or C) while the auxiliary lumen 18A-b may transition outside the reinforcement layer 42 as shown in FIG. 2B at a distal and proximal location (e.g., corresponding to FIG. 2 sections A and D). Additionally, the auxiliary lumen(s) 18A-b may pass through a jacket layer (as described elsewhere herein) overlying the reinforcement layer at or near the point(s) of transition from within to outside of the reinforcement layer 42.

In a further exemplary embodiment, the auxiliary lumen(s) 18A-b may pass through a jacket layer at or near the proximal transition(s) from within to outside the reinforcement layer and may terminate under or within the jacket layer at or near the distal transition(s) from within to outside the reinforcement layer, e.g., such that an actuator wire ring (not shown) with actuator wire(s) (also not shown) attached may be positioned adjacent the distal point(s) of transition with actuator wire(s) travelling through the auxiliary lumen(s) 18A-b over the intermediate portion, the actuator wire ring being positioned under the jacket adjacent the distal transition and the actuator wire(s) exiting the a wall of the shaft through the jacket adjacent the proximal transition(s). A handle, such as that shown in FIG. 1, may be positioned around the proximal exit(s) that includes one or more actuators attached or otherwise coupled to the actuator wires at this position.

With continued reference to FIGS. 2 and 2A-2D, in another exemplary embodiment, a deflectable catheter shaft may be constructed wherein one or more auxiliary lumens 18A-b (e.g., a single auxiliary lumen or two auxiliary lumens spaced approximately one hundred eighty degrees (180°) apart) may be braided under the reinforcement layer 42 as shown in FIG. 2C at an intermediate portion (e.g., corresponding to FIG. 2 sections B and/or C) while the auxiliary lumen 18A-b may transition outside the reinforcement layer 42 as shown in FIG. 2B at a distal and proximal location (e.g., corresponding to FIG. 2 sections A and D). Additionally, the auxiliary lumen(s) 18A-b may pass through a jacket layer (as described elsewhere herein) overlying the reinforcement layer at or near the point(s) of transition from under to outside of the reinforcement layer 42.

In a further embodiment, the auxiliary lumen(s) 18A-b may pass through a jacket layer at or near the proximal transition(s) from under to outside the reinforcement layer and may terminate under or under the jacket layer at or near the distal transition(s) from under to outside the reinforcement layer, e.g., such that an actuator wire ring (not shown) with actuator wire(s) (not shown) attached may be positioned adjacent the distal point(s) of transition with actuator wire(s) travelling through the auxiliary lumen(s) 18A-b over the intermediate portion, the actuator wire ring being positioned under the jacket adjacent the distal transition and the actuator wire(s) exiting the a wall of the shaft through the jacket adjacent the proximal transition(s). A handle, such as that shown in FIG. 1, may be positioned around the proximal exit(s) and one or more actuators may be attached or otherwise coupled to the actuator wires at this position.

FIG. 3 shows another example of catheter 10B, similar to that shown in FIG. 2 except that the auxiliary lumen 18B-b may extend along a proximal portion close to the central lumen 18B-a surrounded by the reinforcement layer 42 (as shown in FIG. 3A), may then transition and extend along an intermediate portion outside the reinforcement layer 42 (as shown in FIG. 3B), may again transition to a location surrounded by the reinforcement layer 42 (as shown in FIG. 3C), and finally may transition to a location outside the reinforcement layer 42 along a distal portion (as shown in FIG. 3D).

Thus, again with general reference to FIGS. 1A and 1B, in any of the apparatus and methods herein, it will be appreciated that the location of the auxiliary lumen 18b and/or reinforcement members 43 of the reinforcement layer 42 may be changed along the length of the apparatus 10 to provide desired mechanical and/or other performance characteristics for the final apparatus.

Figure 5:
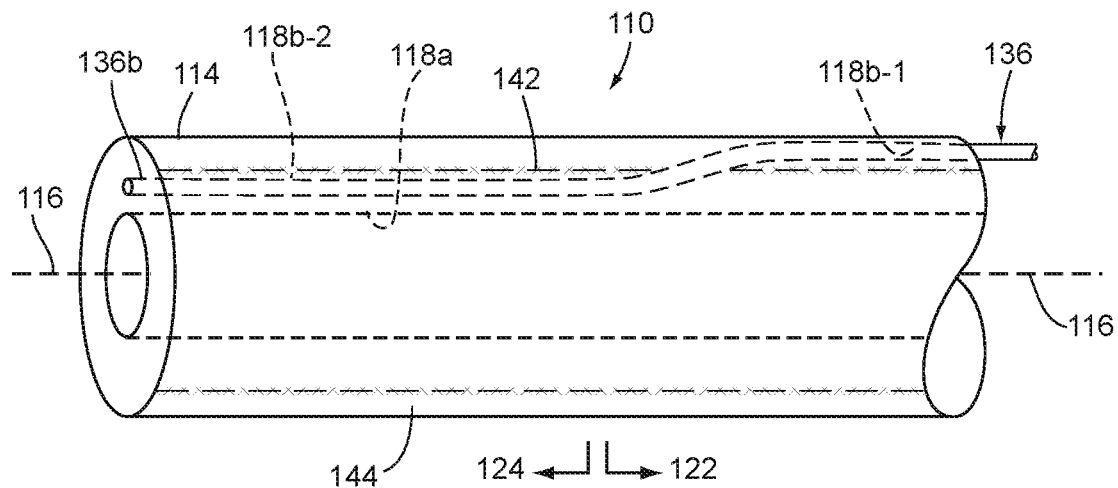
FIG. 5 is a partial cross-sectional side view of an exemplary embodiment of a catheter including a steering lumen for receiving a steering element.
Figure 6:
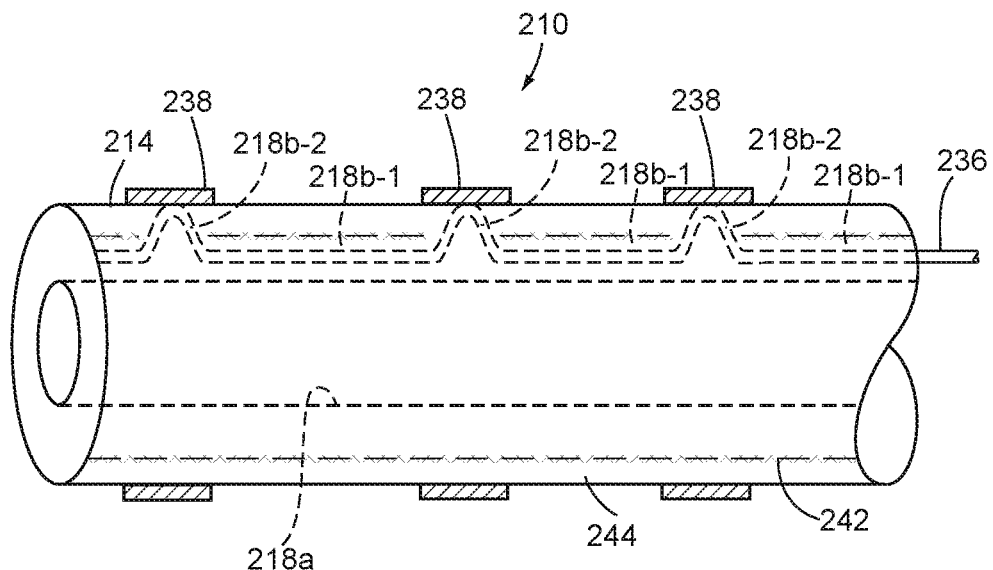
FIG. 6 is a partial cross-sectional side view of another embodiment of a catheter including a plurality of electrodes mounted thereon and including one or more lumens for receiving one or more conductors for coupling to the electrodes.

For example, with reference to FIG. 5, an apparatus 110 is shown in which a distal portion 124 of the apparatus 10 is steerable, e.g., using one or more pull wires, cables, fibers, threads, filaments, or other steering elements, such as a pull wire 136 slidably received within auxiliary lumen 118b. The steering element 136 generally includes a proximal end (not shown) coupled to an actuator, e.g., such as the actuator 34 on the handle 30 shown in FIG. 1, and extends from a proximal portion (not shown) through an intermediate portion 122 and into the distal portion 124. A distal end 136b of the steering element 136 may be fixed or otherwise coupled to the distal end 114, e.g., to a component defining or adjacent the distal tip (not shown).

The steering element 136 may be formed from materials capable of substantially transferring any axial forces applied at the proximal end to the distal end 114, as is known in the art. Optionally, the steering element 136 may include a coating, e.g., PTFE, parylene, silicone, or other lubricious material, an outer sleeve, e.g., formed from HDPE, PTFE, and the like, to reduce friction between the steering element and the wall of the auxiliary lumen 18b. Alternatively or in addition, the inner surface of the auxiliary lumen 118b may be formed from lubricious material and/or may include one or more coatings, as described elsewhere herein. Alternatively or in addition, the auxiliary lumen 18b may include one or more incompressible elements, e.g., a tightly wound coil therearound or therein (not shown), e.g., to prevent compression, which may otherwise lead to creating a bending moment along at least part of its length, e.g., as shown in FIGS. 12-13 and described elsewhere herein.

During use, the actuator may be activated, e.g., directed proximally or distally relative to the handle and/or the proximal end (not shown), to apply an axial force to the steering element 136, e.g., tension (when the steering element is pulled) or compression (when the steering element is advanced). Because the steering element 136 is slidable within the auxiliary lumen 118b, the axial force is translated and applied to the distal end 136b coupled to the distal end 114. Further, because the auxiliary lumen 118b is offset from the central axis 116 along at least the distal portion 124, the axial force applies a bending moment, thereby causing the distal portion 124 to curve or otherwise bend in a desired plane or other manner. Optionally, the proximal and intermediate portions 122 of the apparatus 110 may be constructed to prevent or minimize bending forces caused by actuation of the steering element 136.

In the configuration shown in FIG. 5, along the distal portion 124, a second segment 118b-2 of the auxiliary lumen 118b may be surrounded by the reinforcement layer 142, e.g., immediately adjacent the central lumen 118a (e.g., similar to the location shown in FIG. 3A), and then may transition such that a first segment 118b-1 of the auxiliary lumen 118b is outside the reinforcement layer 142, e.g., closer to an outer surface of the apparatus 110 along at least the intermediate portion 122 (and/or optionally along the proximal portion to the proximal end and/or handle, not shown). Alternatively, the second segment 118b-2 may be braided into the reinforcement layer 142 (e.g., similar to the location shown in FIG. 2A).

Locating the second segment 118b-2 surrounded by the reinforcement layer 142 may enhance performance properties of the steering element 136 and/or may reduce the risk of the steering element 136 tearing through the wall of the distal portion 124, e.g., when a proximal force or tension is applied to the steering element 136. Locating the first segment 118b-1 outside the reinforcement layer 142 may facilitate accessing the auxiliary lumen 118b, e.g., during manufacturing and/or assembly, to couple the proximal end of the steering element 136 to an actuator and/or other components (not shown) at the proximal end of the apparatus 110.

Conversely, if the apparatus 110 were intended to include one or more sensors, actuators, electrodes, imaging element, or other components on the distal portion, the configuration could be reversed. For example, the location of the second segment 118b-2 of the auxiliary lumen 118b may extend from a proximal end of the apparatus 110 to a distal portion and then may transition to the location of the first segment 118b-1, e.g., outside the reinforcement layer 142 along the distal portion. This configuration may facilitate accessing the auxiliary lumen 118b at the distal portion, e.g., to couple one or more wires or conductors disposed within the second segment 118b-2 of the auxiliary lumen 118b to the sensors, actuators, electrodes, imaging elements, and/or or other components, e.g., since the auxiliary lumen 118b is closer to the outer surface of the apparatus 10. Along the proximal and/or intermediate portions, the auxiliary lumen 118b and consequently the conductor(s) may be disposed deeper within the apparatus 110, e.g., beneath and/or within the reinforcement layer 142, which may at least partially shield or otherwise protect the conductor(s).

Turning to FIG. 6, in another embodiment, an apparatus 210 may be provided that includes a plurality of sensors, actuators, electrodes, imaging elements, and/or or other components 238 on a distal portion 224 of the catheter 210, which may be coupled to one or more wires or conductors 236 extending through an auxiliary lumen 218b proximally from the distal portion 224, e.g., to one or more connectors and/or electronics at the proximal end (not shown) of the apparatus 210.

In the exemplary embodiment shown, the auxiliary lumen 218b may extend generally along the distal portion 224 braided into the reinforcement layer (e.g., similar to the location shown in FIG. 2A) or completely surrounded by the reinforcement layer (e.g., similar to the location shown in FIG. 3A) as represented by segments 218b-1, but may transition to segments 218b-2 that are positioned outside the reinforcement layer (e.g., similar to the location shown in FIG. 3B) for a relatively short distance, e.g., under the locations intended for the electrodes 238. With the auxiliary lumen 218b closer to the outer surface at the short segments 218b-2, any wires or conductors within the auxiliary lumen 218b may be easily accessed during manufacturing or assembly, e.g., to expose and couple the electrodes 238 to the conductor(s) when the electrodes 238 are mounted to the distal portion 224. Otherwise, the conductor(s) may be located relatively deep within the apparatus 210.

Alternatively, the lumen configuration shown in FIG. 6 may be adapted to provide a series of side ports in the distal portion 224 in fluid communication with a proximal portion of the catheter (not shown) by way of an unoccupied auxiliary lumen 218b, e.g., such that fluid may delivered through the auxiliary lumen 218b and out the side ports and/or aspirated into the auxiliary lumen 218b through the side ports from a location outside the distal portion 224.

Figure 7A:
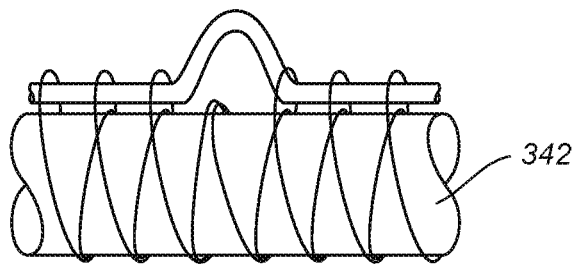
FIG. 7A is a side view of a portion of a catheter subassembly including a primary mandrel and a secondary mandrel wrapped by reinforcement members and including a section of the secondary mandrel that has been pulled outside the reinforcement members.
Figure 7B:
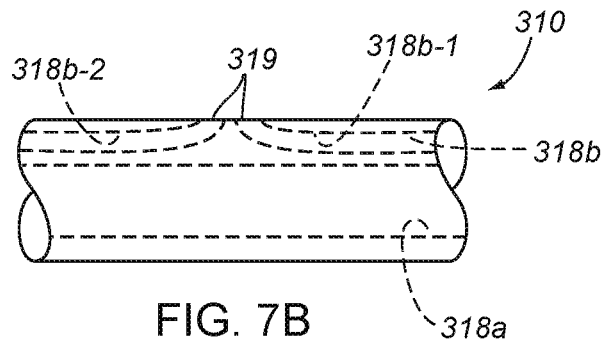
FIG. 7B is a side view of a portion of a catheter resulting from the catheter subassembly of FIG. 7A that includes a discontinuous auxiliary lumen that communicates with side openings in the wall of the catheter.

In yet another embodiment, shown in FIGS. 7A and 7B, an apparatus 310 may be provided that includes a discontinuous auxiliary lumen 318b adjacent a central lumen 318a. For example, as shown in FIG. 7B, a first segment 318b-1 of the auxiliary lumen 318b may extend proximally from a predetermined location, e.g., to a proximal portion of the apparatus 310 and a second segment 318b-2 may extend distally from the predetermined location such that both segments communicate with side openings 319 disposed adjacent one another. The auxiliary lumen 318b may be braided into a reinforcement layer 342, e.g., as shown in FIG. 7A, or disposed at other positions relative to the central lumen 318a, as described elsewhere herein.

Figure 4C:
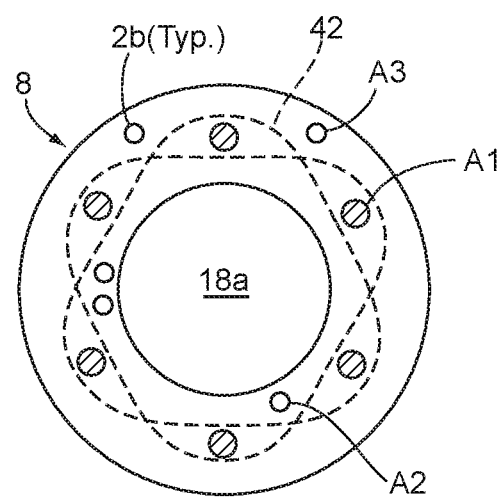
FIG. 4C is a cross-sectional view of a catheter showing the locations of mandrels corresponding to the different locations for the sources of mandrels shown in FIG. 4B.

Turning to FIGS. 4A-4C, various methods may be used for manufacturing and/or assembling any of the embodiments described herein. For example, FIG. 4A shows an exemplary embodiment of an apparatus 50 for making one or more tubular bodies, such as catheters and/or components for catheters, sheaths, or other tubular devices 8. Generally, the apparatus 50 includes a plurality of sources 52, 54 of mandrels 2 and/or liners 4, a guide 60, a source 70 of reinforcement members 6, a drive mechanism 80, and, optionally, a source 90 of jacket material 7.

While mandrels, liners, and/or jackets may be provided in discrete segments (not shown), the apparatus 50 may allow for substantially continuous fabrication of tubular bodies, e.g., wrapping a liner material 4a around a primary mandrel 2a (or the primary mandrel 2a may include a tubular or other liner material provided around it on the source 52, e.g., similar to the liners disclosed in the references incorporated by reference elsewhere herein), positioning an auxiliary mandrel 2b (with optional liner material, not shown) adjacent the primary mandrel 2a, braiding a plurality of reinforcement members 4 around the mandrels 2, and optionally, applying outer jacket material 7 around the reinforced mandrels, as described further below.

As used herein, "substantially continuous" means that the apparatus 50 and/or method may operate indefinitely, i.e., to make as few as one or as many as hundreds or thousands of tubular bodies 8, e.g., by substantially simultaneously feeding components of the tubular bodies 8 from sources 52, such as reels, through components of the apparatus 50 until the sources 52 are depleted, whereupon new source(s) may be loaded onto the apparatus 50 and the process continued. Alternatively, the apparatus 50 may be used to create discrete lengths of tubular devices, e.g., if the mandrels and/or liners are provided in specific lengths corresponding to one or more individual tubular devices (not shown). In a further alternative, some of the operations may be performed substantially continuously, while other operations are performed on components intended for one or more individual tubular devices.

Thus, the apparatus 50 and methods herein may be used to make one or more relatively long tubular bodies 8, e.g., that are substantially longer than finished catheters or other tubular devices. For example, one resulting tubular body 8 may be collected, e.g., on a take-up reel or container (not shown), or may be separated into individual shorter tubular bodies, e.g., using a cutter or other tool (not shown), that may be incorporated into individual catheters or other tubular devices, e.g., as described elsewhere herein and/or as disclosed in U.S. Publication No. 2009/0126862, the entire disclosure of which is expressly incorporated by reference herein.

With particular reference to FIG. 4A, the apparatus 50 may include one or more sources 52 of mandrels 2 and, optionally, one or more sources 54 of liner material 4, which may be fed into a guide 60 to define lumens of the tubular bodies 8. For example, a first reel 52a may include an elongate primary mandrel 2a, e.g., shaped and/or configured to define a primary or central lumen (not shown) of the tubular bodies 8. Similarly, a second reel 52b may include an elongate auxiliary mandrel 2b, e.g., shaped and/or configured to define a secondary or auxiliary lumen (also not shown) of the tubular bodies 8. As described further below, the second reel 52b or other source of auxiliary mandrel may be located at one of a plurality of available locations during operation to configure the tubular bodies 8 in a desired manner. Optionally, if additional lumens are desired for the tubular bodies 8, one or more additional auxiliary mandrels may be provided (not shown), which may also be moved to one or more locations.

The mandrels 2 may have desired cross-sectional shapes and/or sizes corresponding to the desired cross-sections of the lumens, e.g., substantially circular or other shapes, as described elsewhere herein. The mandrels 2 may be a solid or hollow wire or other cylindrical member having a diameter (or other cross-section) corresponding to the diameter of the lumen to be lined by the strip 24, e.g., between about 0.005-0.300 inch (0.125-7.5 mm), 0.014-0.092 inch (0.35-2.3 mm), or 0.014-0.045 inch (0.35-1.15 mm). In an exemplary embodiment, the auxiliary mandrel 2b may have a substantially smaller diameter or other cross-section than the primary mandrel 2a. In exemplary embodiments, the mandrels 2 may be formed from beading or monofilament material, for example, lubricious material, e.g., PTFE or other fluoropolymer, silicone-treated Acetal, PTFE-coated stainless steel, Parylene-coated stainless steel, silver coated copper, and the like, having sufficient flexibility to allow the mandrels 2 to be wound onto a source reel 52 and/or onto a take-up reel (not shown) after being incorporated into a tubular body 8.

Alternatively or in addition, the mandrels 2 may have a tubular liner predisposed about them, e.g., a fluoropolymer sleeve or coating or other tubular material which may facilitate removal of the mandrel 2 and/or be left behind upon removal of the mandrel 2 to form a liner. Further alternatively, a shim (not shown) may be positioned over a mandrel 2 and/or within a tubular or strip liner such that the shim (not shown) may facilitate creation of a lumen that is larger than the mandrel 2 with or without ultimate removal of the mandrel 2. For example, a PTFE tube or strip shim (not shown) may be positioned around a mandrel 2 and inside of a strip or tubular liner. The mandrel/shim/liner assembly may then be incorporated into a braided shaft or finished apparatus. The shim (not shown) may be subsequently removed, e.g., after braiding, lamination, etc., to leave a lumen larger than the mandrel. After this, the mandrel may remain in place, for example in the case of the auxiliary mandrel 2b to serve as a pull wire, or simply removed with less force.

In an alternative embodiment, the mandrels 2 may be formed from material that substantially maintains its size and shape during fabrication of the tubular bodies, yet may be reduced in cross-section after fabrication to facilitate removal. For example, silver-coated copper wire, PTFE beading, or other malleable metals or polymers may be used for the mandrels 2 that, after fabrication of the tubular body 8, may be necked down before and/or during removal. For example, after fabricating a tubular body 8, the mandrels 2 (or the entire tubular body) may be pulled at one or both ends, thereby causing the mandrels 2 to plastically elongate and thereby reduce their outer cross-section slightly, which may reduce friction between the mandrels 2 and the surrounding liners, reinforcement members, and/or other materials, and thereby facilitate removal. Further alternatively, the mandrels 2 may include a rolled strip with inherent radial strength capable of supporting a lumen during braiding and/or lamination and/or other processing, but may subsequently be constrained, stretched, or otherwise removed. Further alternatively, the mandrels 2 may be constructed from material having relatively high thermal expansion such that during heating, lamination, and/or reflow, the mandrels 2 expand and upon cooling contract, thereby creating a lumen larger than the original mandrel 2.

In yet another alternative, the mandrels 2 may be formed from materials that may be dissolved, e.g., after fabrication, leaving the surrounding materials intact to define the lumens.

In still another alternative, tubular mandrels may be used that have sufficient hoop strength to resist deformation under the forces encountered during braiding and/or other fabrication and/or heating or other processing parameters experienced during fabrication. In this alternative, the tubular mandrels may remain substantially within the tubular bodies 8 after fabrication, e.g., to define the auxiliary lumen. For example, a relatively thick walled PTFE, a lined or bare polyimide tube, or other tubular mandrel may be used. Alternatively, the inner diameter of such a tubular mandrel may be temporarily supported by a temporary supporting mandrel (not shown), e.g. during braiding, and the temporary supporting mandrel may be removed prior to subsequent fabrication and/or heating or other processing steps, e.g., if the tubular mandrel is to remain as a permanent component of the tubular bodies.

Optionally, a source 54 of liner material 4 may be provided for the one or both mandrels 2. For example, as shown, a source 54a of liner material 4a is provided such that the liner material 4a may be wrapped at least partially around the primary mandrel 2a, e.g., as the primary mandrel 2a and liner material 4a are fed through the guide 60. The liner material 2a may be formed from lubricious material and/or may include one or more coatings (not shown) on an inner surface thereof oriented towards the primary mandrel 2a, which may provide an inner liner for a primary lumen of the resulting tubular bodies 8a.

For example, the liner material may include a base material, e.g., a relatively thin-walled polymer sheet having a width corresponding to the circumference of the corresponding mandrel, e.g., thermoplastics, such as polyether block amide, urethane, nylon, and the like, fluoropolymers, such as PTFE, FEP, TFE, and the like, thermoset, and thermoform plastics, such as polyimide or polyester, and the like. In exemplary embodiments, the liner material may have a thickness between about 0.0001-0.050 inch (0.0025-1.25 mm), 0.0001-0.003 inch (0.0025-0.076 mm), 0.0001-0.0015 inch (0.0025-0.038 mm), or 0.0005-0.002 inch (0.0125-0.05 mm).

Optionally, if desired a source of liner material may also be provided for the auxiliary mandrel 2b and/or for other auxiliary mandrels (not shown for simplicity). In this option, a guide (not shown) may be provided for wrapping the liner material around the auxiliary mandrel 2b, e.g., before the auxiliary mandrel 2b is positioned adjacent the primary mandrel 2a. In an alternative embodiment, tubular liner material may be provided on one or both mandrels s when loaded on the source 52, and/or may be fed onto the desired mandrel in discrete segments (not shown) before passing the mandrels 2 through the guide 60 or horn gear 72.

With additional reference to FIGS. 4A and 4B, the source 70 of reinforcement members 6 may provide one or more, e.g., a plurality of, reinforcement members 6 that may be wrapped around the mandrels 2, e.g., upon exiting the guide 60. In the exemplary embodiment shown in FIG. 4B, the reinforcement source 70 may include an arrangement of horn gears 72, e.g., mounted in a generally circular configuration around the guide 60, for example, to a base or other support structure 76. The horn gears 72 may be free to rotate about their individual central axes but may be substantially fixed translationally relative to one another and the guide 60. The horn gears 72 may pass one or more carriers 74 of reinforcement members 6 around the path 78, e.g., in a clockwise and/or counterclockwise direction, e.g., with at least some of the carriers travelling clockwise and some travelling counterclockwise, e.g., to create a braided pattern. The carriers 74 may be loaded onto the horn gears to create a variety of patterns, e.g., one-over-one-under (diamond pattern), two-over-two-under (herring bone pattern), one-over-one-under with two reinforcement members running side by side (tow), and/or other patterns, as are known in the art.

Alternatively, the horn gears 72 may be rotatable relative to the guide 60 and/or primary mandrel 2a, e.g., around a central axis of the guide 60, e.g., along a path 78 shown in FIG. 4B, while maintaining their same circular configuration, e.g., by rotating the base 76 relative to the guide 60, as described further elsewhere herein.

In addition, the auxiliary mandrel 2b may be moved to different locations relative to the horn gears 72, e.g., to position the auxiliary mandrel 2b relative to the primary mandrel 2a and/or reinforcement members 6. For example, as shown in FIG. 4B, during operation of the apparatus 50, the source of auxiliary mandrel 2b may be positioned at locations A1, A2, or A3, e.g., for a predetermined time and/or distance along the primary mandrel 2a, and, as desired, moved to one of the other locations one or more times. Thus, in this manner, the location of the auxiliary mandrel 2b may be adjusted, which may result in the location of an auxiliary lumen defined by the auxiliary mandrel 2b being moved to desired locations, as shown in FIG. 4C and as described elsewhere herein.

For example, in position A1 shown in FIG. 4A, one of the horn gears 72a may include a passage 73a therethrough, e.g., aligned with the central axis of the horn gear 72a, and the auxiliary mandrel 2b may pass through the passage 73a, e.g., from the source 52b towards the primary mandrel 2a where it exits the guide 60. If liner material is wrapped or otherwise disposed around the auxiliary mandrel 2b, a guide (not shown) may be provided before, after, or within the passage 73a to wrap or otherwise dispose the liner material around the auxiliary mandrel 2b. Optionally, if additional auxiliary lumens are to be provided in the tubular bodies 8, one or more additional horn gears may also include such passage(s) and/or guide(s) for guiding corresponding auxiliary mandrel(s) therethrough.

As described further below, in this location, the auxiliary mandrel 2b may be at least partially braided into the reinforcement members 6 adjacent the primary mandrel 2a, i.e., with some reinforcement members 6 surrounding both the primary mandrel 2a and the auxiliary mandrel 2b, and some reinforcement members 6 surrounding only the primary mandrel 2a, as identified by auxiliary mandrels A1 shown in FIG. 4C. By comparison, in location A2, i.e., with the auxiliary mandrel 2b directed immediately adjacent the primary mandrel 2a, e.g., through the guide 60, all of the reinforcement members 6 may surround both the primary mandrel 2a and the auxiliary mandrel 2b, thereby positioning the auxiliary mandrel 2b closest to the primary mandrel 2a along the tubular device 8. Finally, in location A3, i.e., with the auxiliary mandrel 2b outside the path of the horn gears 72, e.g., outside the path 78 shown in FIG. 4B, or otherwise directed towards the primary mandrel 2a after the braiding operation, all of the reinforcement members 6 may only surround the primary mandrel 2a and the auxiliary mandrel 2b may remain outside all of the reinforcement members 6, e.g., closest to the outer surface of the tubular device 8 shown in FIG. 4C.

Optionally, if desired, individual carriers may be loaded with multiple reinforcement members (not shown), e.g., such that multiple reinforcement members are braided adjacent one another in each direction from each carrier. For example, with the auxiliary mandrel 2b directed from location A1, a first set of reinforcement members 43a may travel and be braided in a first direction by the horn gears 72 such that all of the windings of the first set 43a pass between the auxiliary mandrel 2b and the primary mandrel 2a at that specific horn gear. A second set of reinforcement members 43b may travel and be braided in a second opposite direction by the horn gears 72 such that all of the windings of the second set 43b pass over the auxiliary mandrel 2b at that specific horn gear. Otherwise, the reinforcement members may pass over and under one another according to the arrangement of horn gears 72 and carriers 74 loaded onto the reinforcement source 70, which pattern generally alternates at each subsequent horn gear, e.g., as described in U.S. Publication No. 2014/0323964, incorporated by reference herein.

In addition, with the auxiliary mandrel 2b in position A1, one of the horn gears 72a may include a passage 73a therethrough, e.g., aligned with the central axis of the horn gear 72a, and the auxiliary mandrel 2b may pass through the passage 73a, e.g., from the source 52b towards the primary mandrel 2a where it exits the guide 60. If liner material is wrapped or otherwise disposed around the auxiliary mandrel 2b, a guide (not shown) may be provided before, after, or within the passage 73a to wrap or otherwise dispose the liner material around the auxiliary mandrel 2b.

Optionally, if additional auxiliary lumens are to be provided in the tubular bodies 8, one or more additional horn gears may also include such passage(s) and/or guide(s) for guiding corresponding auxiliary mandrel(s) therethrough, e.g., to provide auxiliary mandrel(s) in location A1, or additional auxiliary mandrel(s) may be provided at locations A2 and/or A3, as desired.

With further reference to FIG. 4A, as can be seen, the primary mandrel 2a may exit the guide 60 with the liner material 4a being wrapped substantially around the primary mandrel 2a. With the auxiliary mandrel 2b directed from the desired location, the auxiliary mandrel 2b may be directed towards the primary mandrel 2a such that the auxiliary mandrel 2a is disposed adjacent the primary mandrel 2a, e.g., before braiding (location A2), braided into the reinforcement members 6 (location A1), or after braiding (location A3).

At any time, the auxiliary mandrel 2b may be moved to a different location than its current one to transition the auxiliary mandrel 2b to the desired position relative to the primary mandrel 2a and/or reinforcement members 6. Thus, in this manner, all of the reinforcement members 6 may surround the primary mandrel 2a, while all, some, or none of windings 43a may surround the auxiliary mandrel 2b, as shown in FIG. 4C. This transition may be performed substantially continuously, e.g. by directing the auxiliary mandrel 2b to the desired location after a predetermined length or portion of the tubular device 7 has been braided in the desired manner. Alternatively, discrete lengths or portions may be braided in the desired manner, e.g., by stopping the apparatus 50, removing and repositioning the auxiliary mandrel 2b to position the auxiliary mandrel 2b to the desired relative to the primary mandrel 2a and/or reinforcement members 6, and then resuming operation for a desired time and/or length. This process may be repeated as many times as desired, e.g., to produce tubular devices, such as the apparatus 10A, 10B shown in FIGS. 2 and 3.

Returning to FIGS. 4A and 4B, the drive mechanism 80 may include one or more components for pulling or otherwise directing the mandrels 2 through the apparatus 50. For example, the drive mechanism 80 may include a pair of spaced-apart rollers 82 coupled to a motor (not shown) that engage the reinforcement-wrapped mandrels 2 and apply sufficient tension to pull the mandrels 2 from their sources 52 through the guide 60 and/or horn gear 72a while the reinforcement members 6 are braided around the mandrels 2. Alternatively, the drive mechanism may be provided before the reinforcement members 6 are braided around the mandrels 2, e.g., pushing the primary mandrel 2a through the braiding operation and potentially pulling the auxiliary mandrel 2b by the braiding action itself. Optionally, other drive mechanisms and/or tension adjusters (not shown) may be provided for maintaining a desired tension and/or otherwise guiding the mandrels 2, liners 4, reinforcement members 6, and assembled device in a desired manner along the fabrication path.

Optionally, as shown in FIG. 4A, the jacket source 90 may be provided for applying one or more layers of jacket material around the reinforcement-wrapped mandrels 2. For example, a co-extruder, laminator, or other applicator may be provided that applies melted, uncured, and/or otherwise raw jacket material 7, e.g., from a hopper or other container (not shown), or rolls sheets of jacket material 7 may be wrapped around the reinforcement members 43 and mandrels 2. For example, for thermoplastic or other flowable materials, a heater (not shown) within a co-extruder may melt or otherwise soften the jacket material 7 to allow the jacket material 7 to flow around the reinforcement members 43 and into contact with the liner material 4 surrounding the mandrels 2 (or the mandrels 2 directly if no liner material is provided). Alternatively, the jacket material 7 may be a thermoset plastic or other material such that components of the jacket material 7 may be delivered into the co-extruder, e.g., as a liquid, powder, and the like, and mixed to form a slurry that is delivered around the reinforcement-wrapped mandrels 2. The components may chemically or otherwise react with one another and/or be heat fused to form a solid jacket 7 once cured. Exemplary materials for the jacket material 7 include plastics, e.g., thermoplastics, such as polyether block amide, nylon, or urethanes, thermoset plastics, metals, or composite materials. Alternatively, other processing may be used to bond or otherwise attach the jacket material 7 to the liner material 4 and/or embed the reinforcement members 43 in the jacket material 7, thereby resulting in an integral tubular body 8.

The resulting tubular body 8 (with or without jacket material 7) may be collected, e.g., on a capture reel or in a container (not shown). Thereafter, the tubular body 8 may be further processed to make a catheter, sheath, or other device. For example, a cutter or other tool (not shown) may separate the tubular body 8 into individual tubular shafts, e.g., before or after removing the mandrels 2. For example, the mandrels 2 may remain within the tubular body 8 when cut into individual devices, and then may be removed, resulting in a primary lumen and an auxiliary lumen, e.g., similar to the apparatus 10 shown in FIG. 1B. Alternatively, if the friction between the mandrels 2 and the surrounding material is relatively low, the mandrels 2 may be removed before the tubular body 8 is cut into individual devices.

The resulting inner surface 41a of the primary lumen 18a may have a substantially uniform cross-section, e.g., as shown in FIG. 1B. Similar the auxiliary lumen 18b may also have a substantially uniform cross-section, e.g., also as shown in FIG. 1B or may have a variable cross-section, if desired (not shown).

Other components may be added to the individual tubular devices, as desired for the particular application. For example, for a steerable catheter, such as the apparatus 110 shown in FIG. 5, a steering element 136 may be inserted through the auxiliary lumen 118b (created when the auxiliary mandrel 2b is removed). In an alternative embodiment, the auxiliary mandrel 2b may remain within the tubular device to provide the steering element, e.g., if the friction between the outer surface of the auxiliary mandrel 2b and the liner or other material defining the auxiliary lumen are relatively low. A tip or other component (not shown) may be attached to a distal end 114 of the apparatus 110, e.g., after attaching the distal end 136b of the steering element 136 to the tip. The other end of the steering element may be coupled to an actuator of a handle attached to a proximal end of the tubular device, e.g., similar to the embodiment shown in FIG. 1A and described elsewhere herein.

For the apparatus 210 shown in FIG. 6, the auxiliary lumen 218b may be formed by positioning the auxiliary mandrel 2b in location A2 (shown in FIGS. 4B and 4C or optionally in location A1 for at least some portions) and generally braiding the reinforcement material 6 around both the primary and auxiliary mandrels 2a, 2b, except that at the segments corresponding to the locations of the electrodes 238, the auxiliary mandrel 2b may be moved to location A3 and then returned back to location A2 (or A1). After the outer layer 244 has been applied around the reinforcement members 242, the mandrels may be removed to provide an auxiliary lumen with segments 218b-1 braided into or under the reinforcement layer 242 other than segments 218b-2 at the electrode locations.

One or more wires 236 may be directed into the auxiliary lumen 218b (or may be used as the auxiliary mandrel, if desired), and the segments 218b-2 may be accessed, e.g., by cutting into the outer layer 244 to expose the wire(s), which may then be coupled to the electrodes 238 mounted on the apparatus 210.

Alternatively, the auxiliary mandrel 2b may remain at location A2 (or A1) for the entire length of the tubular body 8, and a segment of the auxiliary mandrel 2b may be manually (or automatically) pulled out from within the braid of the reinforcement members 6, as shown in FIG. 7A before applying the outer layer 244. In this alternative, the auxiliary lumen 318b may be discontinuous, i.e., communicating with side openings 319. One or more wire(s) may be directed into the auxiliary lumen 318b such that regions of the wire(s) exit and reenter the side openings 319. These regions may then be exposed and/or otherwise coupled to an electrode (not shown) mounted on the apparatus 310.

Figure 8A:
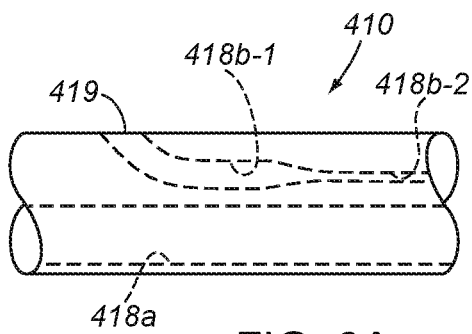
FIG. 8A is a side view of a portion of another embodiment of a catheter including an auxiliary lumen that has a variable diameter.
Figure 8B:
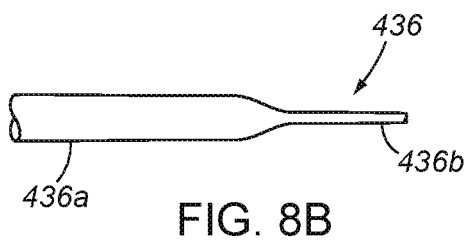
FIG. 8B is a side view of a portion of a steering element that may be received in the auxiliary lumen of the catheter of FIG. 8A.

Turning to FIGS. 8A and 8B, optionally, in any of the embodiments herein, the size of the auxiliary lumen 418b may be varied at desired locations along the apparatus 410, e.g., by using an auxiliary mandrel having a variable diameter or other cross-section (not shown). For example, in the apparatus 410 shown in FIG. 8A, an auxiliary lumen 318b is provided adjacent a central lumen 318a, which may be positioned relative to the central lumen 318a and/or reinforcement members (not shown), similar to other embodiments herein. As shown, the auxiliary lumen 418b includes a first or proximal segment 318b-1 having a first diameter and extending from a side opening 319 along a portion of the apparatus 410. The auxiliary lumen 418b then transitions to a second segment 418b-2 having a second diameter smaller than the first diameter.

Such an auxiliary lumen 418b may be formed using an auxiliary mandrel having regions corresponding to the first and second diameters and lengths of the segments. As shown in FIG. 8B, a steering element 436 may be provided that has similar diameters and regions (e.g., slightly smaller than the first and second diameters). After removing the auxiliary mandrel, the steering element 436 may be loaded into the auxiliary lumen 418b through the side opening 419 and the distal segment (not shown) may be coupled to the distal end of the apparatus 410, similar to other embodiments herein. Alternatively, the auxiliary mandrel itself may be used as the steering element, also similar to other embodiments herein. This configuration may enhance pushability of the apparatus 410, e.g., since the proximal, larger segment may be relatively stiffer than the distal, smaller segment.

Figure 9:
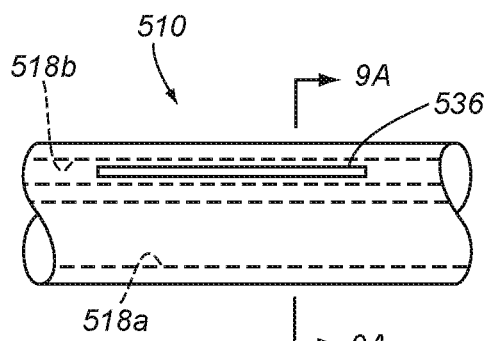
FIG. 9 is a side view of a portion of still another embodiment of a catheter including one or more stiffening elements embedded into a wall of the catheter.
Figure 9A:
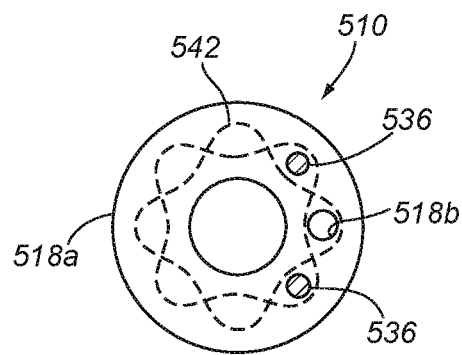
FIG. 9A is a cross-section of the catheter of FIG. 9 taken across 9A-9A.

Optionally, in any of the embodiments herein, one or more stiffening members may be added to desired portions of the apparatus. For example, FIGS. 9A and 9B show an exemplary embodiment of an apparatus 510 including a central lumen 518a and auxiliary lumen 518b, which may be surrounded and/or braided into a reinforcement layer 542, similar to other embodiments herein.

Unlike previous embodiments, a pair of stiffening members 536 have also been braided into the reinforcement layer 542. For example, with reference to the apparatus 50 in FIGS. 4A-4C, at desired portions of the tubular body 8, one or more stiffening members (not shown) may be directed adjacent the primary mandrel 2a, e.g., at positions similar to A1 (to braid the stiffening members into the reinforcement members 6. In this manner, the supported portion(s) may have greater column strength than other unsupported portions of the resulting apparatus 510.

Figure 10:
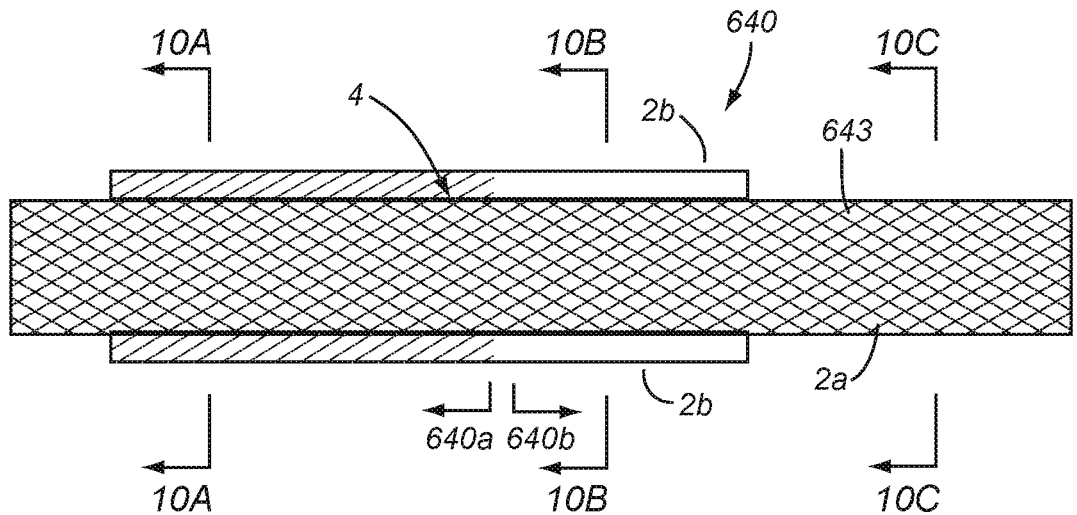
FIG. 10 is a side view of a mandrel/reinforcement subassembly including a pair of secondary mandrels partially braided into a length of the subassembly.
Figure 11A:
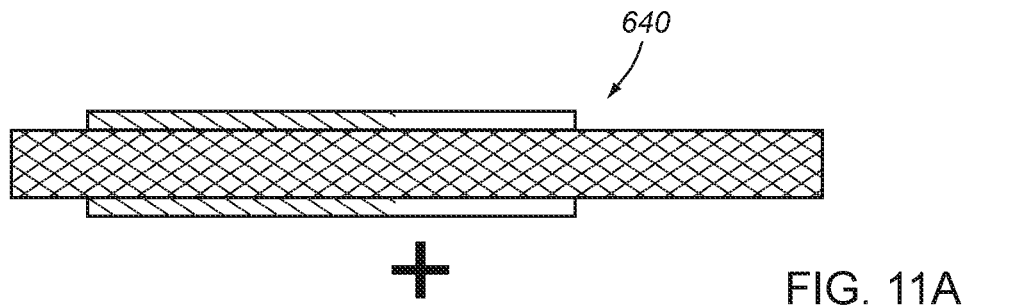
FIGS. 11A-11J show an exemplary method for making a steerable catheter including a lapped braid with a pull wire ring.
Figure 11B:
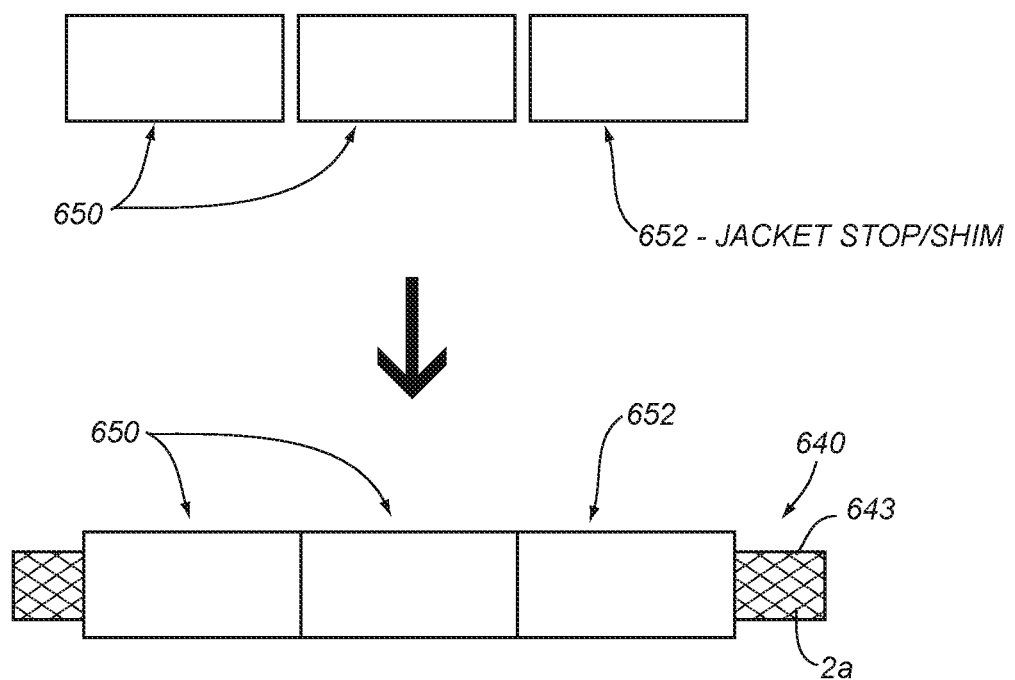
Figure 11C:
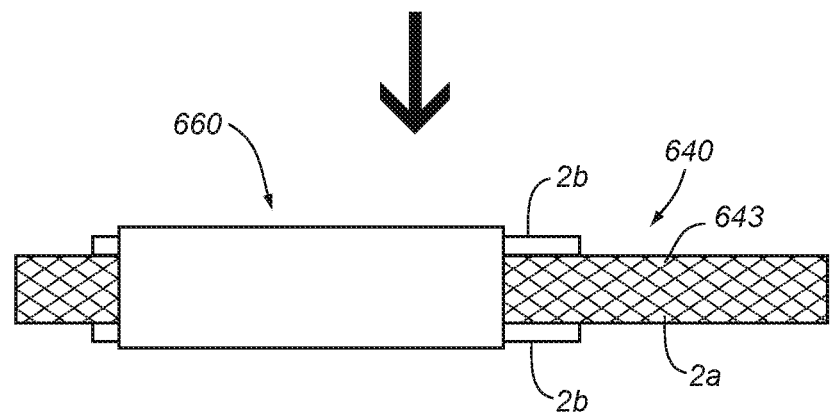
Figure 11D:
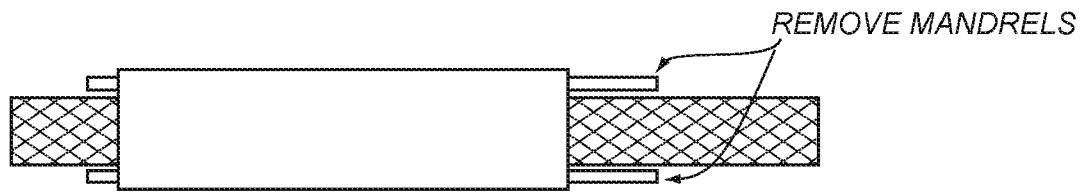
Figure 11E:
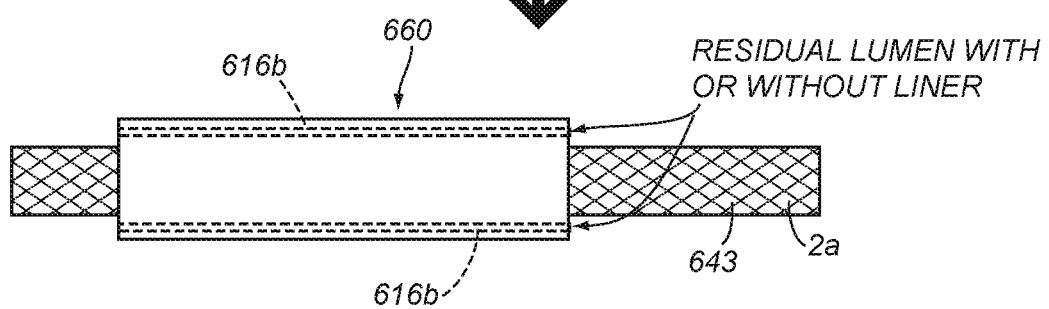
Figure 11F:
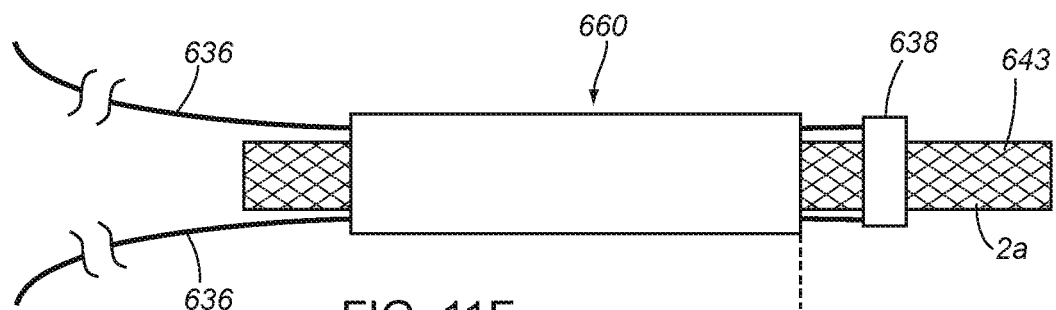
Figure 11G:
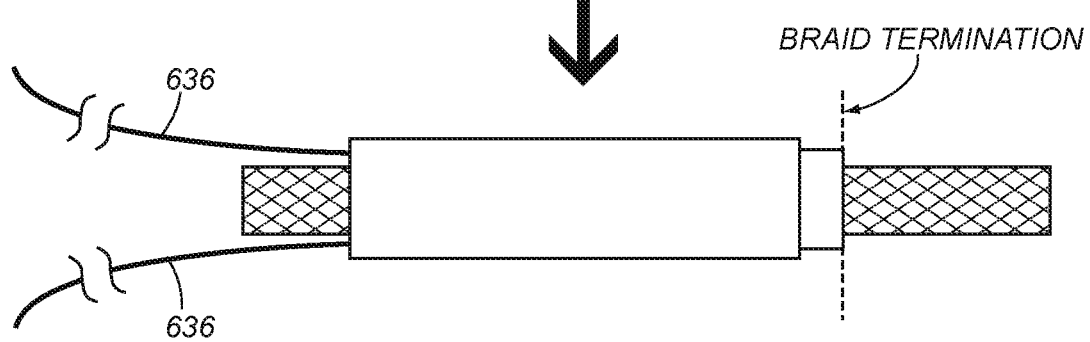
Figure 11H:
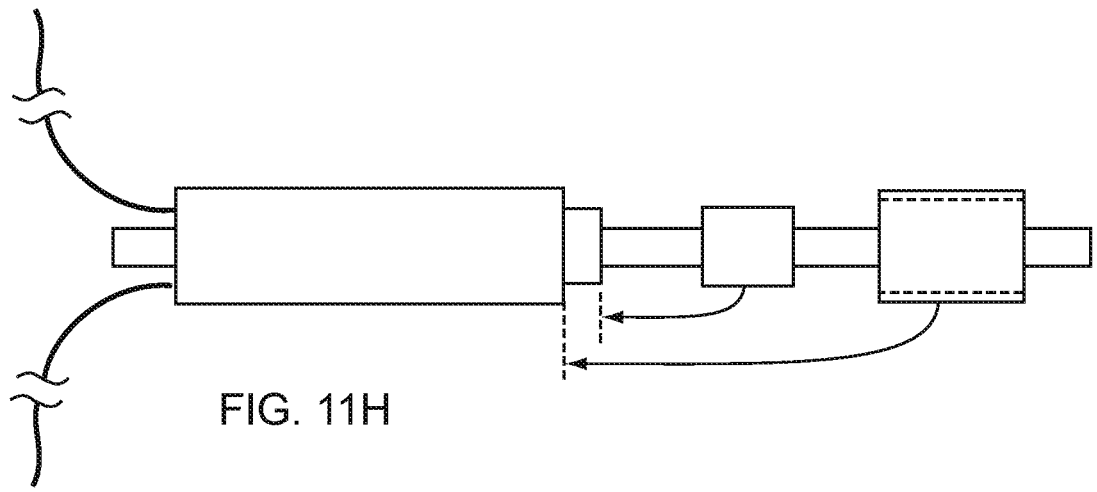
Figure 11I:
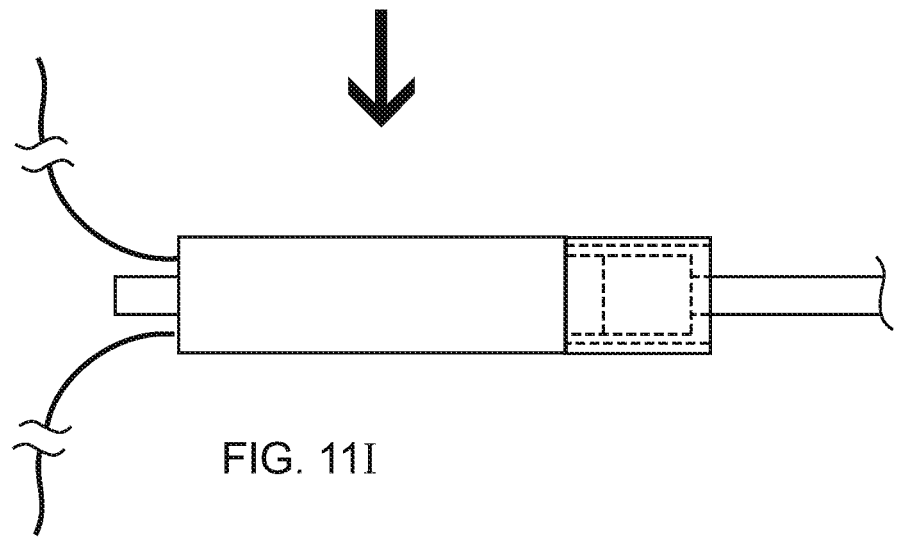
Figure 11J:
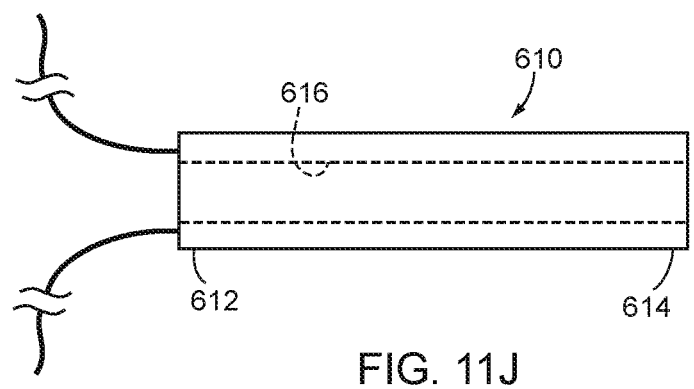

Turning to FIGS. 10-11J, an exemplary method for making a steerable catheter 610 (best seen in FIG. 11J) that generally includes a proximal end 612, a distal end 614, and one or more lumens 616 extending therebetween, similar to other embodiments herein. For example, as shown in FIG. 11J, the catheter 610 includes a central or primary lumen 616a and a pair of steering lumens 616b slidably receiving respective pull wires 636 coupled to a pull wire ring 638 adjacent the distal end 614. The catheter 610 may be fabricated using similar materials and methods to the previous embodiments, e.g., using a braiding apparatus, similar to that shown in FIGS. 4A and 4B.

Figure 10A:
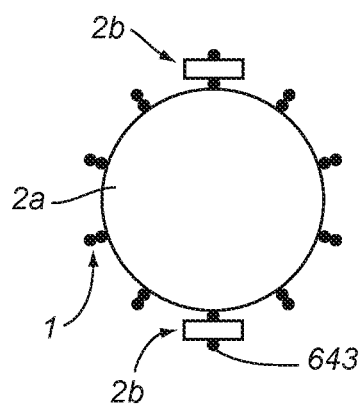
FIGS. 10A-10C are cross-sectional views of the subassembly of FIG. 10 taken along sections 10A-10A, 10B-10B, and 10C-10C, respectively.

For example, turning to FIG. 10, a mandrel/reinforcement subassembly 640 may be made by braiding a plurality of reinforcement members 643 around a primary mandrel 2a and at least partially around a pair of secondary mandrels 2b, e.g., with the location of the secondary mandrels 2b being changed in a predetermined manner along the length of the subassembly 640. In the exemplary embodiment shown, along a first portion 640a of the subassembly 640, e.g., corresponding to an intermediate and/or proximal portion of the catheter 610, the secondary mandrels 2b are braided into the reinforcement members 643, e.g., such that some of the members 643 are disposed between the primary and secondary mandrels 2a, 2b, and some members surround both the primary and secondary mandrels 2a, 2b, as shown in FIG. 10A.

Figure 10B:
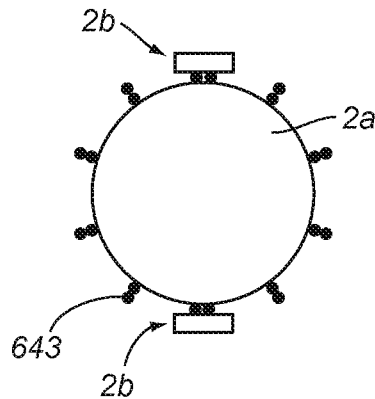
Figure 10C:
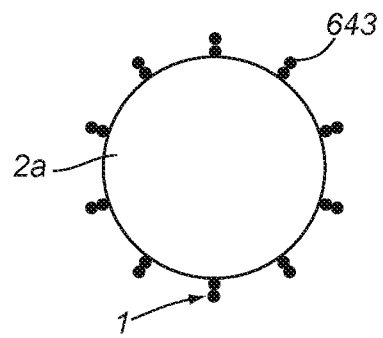

At a second portion 640b, e.g., corresponding to a distal portion of the catheter 610, the secondary mandrels 2b transition such all of the reinforcement members 643 are braided around only the primary mandrel 2a, as shown in FIG. 10B. Braiding of the reinforcement members 643 may continue beyond the ends of the secondary mandrels 2b, e.g., as shown in FIG. 10C.

One or more outer layers may then be applied around the subassembly 640 to provide the final catheter 610. For example, as shown in FIG. 11A, a plurality of tubular jackets 650 may be applied around the subassembly 640, e.g., having different materials and/or mechanical properties, as desired for the different portions of the catheter 610. The jackets 650 may be sized to have the subassembly 640 inserted into them such that they abut or are otherwise disposed adjacent one another around the subassembly 640. In addition, a tubular jacket and/or shim 652 (where at least the outer part of the shim 652 is ultimately removable) may be positioned around the subassembly 640, e.g., around the portion 640b such that the shim 652 at least partially covers the unconstrained ends of the secondary mandrels 2b.

Subsequently, the resulting assembly 660 may be reflowed, heated, and/or otherwise laminated, e.g., similar to other embodiments described elsewhere herein. The shim 652 may then be removed, as shown in FIG. 11C, and then the mandrels 2b may also be removed, as shown in FIGS. 11D and 11E. As shown in FIG. 11E, a shoulder 664 (at the right of the assembly 660) remains at the junction between the tubular jackets 650 and the removed shim 652 with the lumens 616b created by removal of the secondary mandrels 2b exiting from the face of the shoulder 664 in a position radially outward from the reinforcement members 643 present in the portion 640b.

Turning to FIG. 11F, a pull wire ring 638 having pull wires 636 extending from its proximal edge may then be inserted over the portion 640b with the pull wires 636 may be loaded into the lumens 616b. For example, distal ends 636b of the pull wires 636 may be attached to the proximal edge of the ring 638, e.g., by welding, soldering, bonding with adhesive, and the like before the ring 638 is inserted over the portion 640b. This allows the pull wires 636 to be inserted into the auxiliary lumens 616b (not shown in FIG. 11F; see, e.g., FIG. 11E) without taking a substantial bend and the pull wire ring 638 may abut the shoulder 664.

As shown in FIG. 11G, the reinforcement members 643 may then be trimmed at or near the distal edge of the pull wire ring 638 with the pull wire ring constraining the reinforcement members 643 such that, as shown in FIG. 11I, a subsequent a jacket and or tip may be bonded, laminated, reflowed or otherwise attached over and/or beyond the pull wire ring 638 without risk of the reinforcement members 643 rising to or protruding through the surface. Using this method, tip defects may be minimized, stress on the pull wire may be minimized, and/or the assembly may be otherwise considerably improved.

Optionally, the pull wire ring 638 may include one or more features (e.g., holes, slots, etc. not shown) to enhance attachment to the catheter shaft, tip, etc. In addition or alternatively, a thermoplastic liner (e.g., with a coating, similar to other embodiments herein) may be provided on the distal end to enable discrete tip sections to be added and subsequently laminated creating a highly manufacturable device with a completely contiguous/welded liner surface with no edges, discontinuities, or potential for delamination, skiving, leakage, and the like.

Configuring the ring 638 and/or tip jacket components in this manner may provide one or more advantages. For example, lapping the braid or reinforcement layer into and through the ring 638 may eliminate a common kink point that may be a limitation with current devices. In addition, this configuration may eliminate problems with cut end wire protrusions as they are full constrained within the ring 638. In addition, this configuration may provide locations for pull wire lumens that substantially align with desired positions of pull wires, which may ease assembly, enhance integrity of the tip, and/or improve alignment of pull forces.

Turning to FIGS. 12-13, another exemplary embodiment of a steerable catheter 708 is shown that generally includes a tubular body or shaft 710 including a proximal end 712, a distal end 714 sized for introduction into a patient's body, and one or more lumens 718 extending therebetween, which may be constructed using similar materials and methods as other embodiments described herein. For example, as shown in FIGS. 13-13D, the tubular body 710 may include a primary lumen 718a and one or more auxiliary lumens, e.g., a steering element lumen 718b offset from a central longitudinal axis 716 of the tubular body 710, e.g., close to the outer periphery of the tubular body 710, that slidably receives a pull wire or other steering element 736.

Also similar to other embodiments herein, a handle or hub 730 may be provided on the proximal end 712 of the tubular body 710, e.g., including one or more ports 732 communicating with the central lumen 718a or other respective lumens (not shown). For example, port 732a may include one or more valves, e.g., a hemostatic valve (not shown), which may provide a substantially fluid-tight seal, while accommodating insertion of one or more instruments or fluids into the central lumen 718a. Optionally, a side port 732b may also be provided, e.g., for delivering fluid into and/or aspirating fluid from the primary lumen 718a, e.g., around an instrument inserted into the primary lumen 718a.

In addition, the handle 730 may include one or more actuators, such as sliders, buttons, switches, rotational actuators, and the like, e.g., for activating and/or manipulating components (also not shown) on the distal end 714 or otherwise operating the catheter 708. For example, as shown in FIG. 12, an actuator 734 may be provided that is coupled to a proximal end 736a of the steering element 736 disposed within the auxiliary lumen 718b, e.g., similar to other embodiments described elsewhere herein. As described elsewhere herein, the steering element 736 may be actuated, e.g., axially pushed or pulled, to apply a bending force to a distal portion 724 of the tubular body 710, e.g., to cause the distal portion 724 to curve, bend, or otherwise deflect in a desired manner.

Unlike previous embodiments, a compression-resistant element 746 is disposed within the steering element lumen 718b surrounding or otherwise adjacent at least a portion of the steering element 736, e.g., extending from the proximal end 712a of the tubular body 710 through an intermediate portion 722, i.e., terminating at the distal portion 724, to prevent forces from the steering element 736 from transferring to the tubular body 710 proximal to the distal portion 724. As can be seen in FIG. 13A, the compression-resistant element 746 may be sized to slide within the steering element lumen 718b and/or slidably receive the steering element 736 therethrough, e.g., thereby preventing bending forces from the steering element 736 being transferred to the tubular member material surrounding the steering element lumen 718b along portion(s) where the compression-resistant element 746 is provided.

In an exemplary embodiment, the compression-resistant element 746 may be a tightly-wound coil, e.g., with coils abutting one another in a relaxed or low potential energy state, such that the coil cannot be compressed axially. In exemplary embodiments, the coil 746 may be formed from metal, steel, polymers, or composite materials, e.g., one or more stainless steel or Nitinol wires having a round or rectangular cross-section. Alternatively, other tubular or cylindrical structures may be provided for the compression-resistant element 746, which may be slidably received within the steering element lumen 718b and slidably receive the steering element 736 therethrough. For example, in other embodiments, the compression-resistant element 746 may include a counter-wound coil tube, a coil tube with one or more attached tensile elements, a laser cut tube, a densely braided polymer tube, and the like (all not shown).

The coil 746 may be free floating or otherwise slidably received within the steering element lumen 718b, e.g., with proximal and distal ends 746a, 746b thereof remaining uncoupled to the tubular body 710. Alternatively, one or both ends may be fixed or stopped relative to the tubular body 710, e.g., by one or more of embedding the end(s) within the tubular body, bonding with adhesive, heat welding, sonic welding, incorporation of a secondary stop element, and the like. In an exemplary embodiment, the coil may be fixed at its distal end with an additional stop for reinforcement whereas the proximal end may be left free to slide both along the length and into and out of the steering element lumen such that path length changes of the steering element lumen due to manipulation of the catheter may be accommodated without transferring these forces to the tubular body 710. For example, FIG. 13B shows the distal end 746b of the coil 746 fixed relative to the tubular body 710.

The proximal end 746a of the coil 746 may be free to move within the handle 730 while still coupled to the actuator 734. In addition or alternatively, the coil 746 may include a loop or helical section (not shown) within the interior of the handle 730, e.g., around the primary lumen shaft, i.e., between the proximal end 712 of the tubular body 710 and where the proximal end 746 is coupled to the handle 730 adjacent the actuator 734. Thus, the proximal end 736a of the steering element 736 may exit the fixed proximal end 746a of the coil 746 and then be coupled to the actuator 734. If both ends of the coil 746 are fixed relative to the tubular body 710 (while the intermediate length is free to slide within the steering element lumen 718b, the coil 746 may resist axial extension as well as compression along the side of the tubular body 710 surrounding the steering element lumen 718b.

Figure 14:
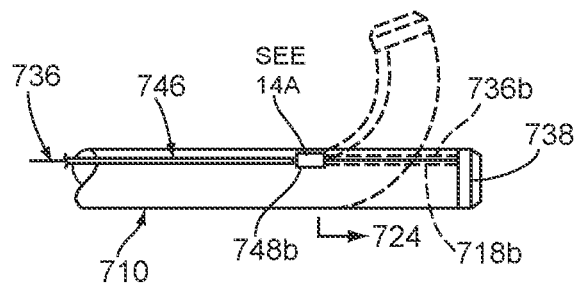
FIG. 14 is a cross-sectional view of a distal portion of the tubular body of FIG. 13, showing an exemplary embodiment of a distal stop that may be provided adjacent the compression-resistant coil.
Figure 14A:
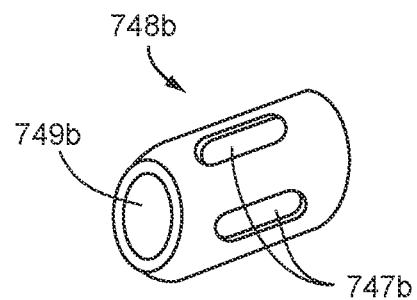
FIG. 14A is a detail of an exemplary embodiment of the distal stop of FIG. 14.

Optionally, as shown in FIG. 12, one or more stops 748 may be provided adjacent one or both ends 746a, 746b of the coil 746 for limiting movement of the end(s). For example, as shown in FIGS. 12 and 14, a distal stop 748b may be provided adjacent the distal end 746b of the coil 746, e.g., fixed within or across the steering element lumen 718b. FIG. 14A shows an exemplary embodiment of a stop 748b that includes a passage 749b therethrough for slidably receiving the steering element 736, e.g., such that the steering element 736 may continue through the distal portion 724 to a ring or other anchor 738 on the distal end 714 of the tubular body 710, e.g., as shown in FIGS. 13C, 13D, and 14. However, the stop 748b may be sized such that the distal end 746b of the coil 746 may abut or otherwise contact the stop 748b, e.g., when the region adjacent the steering element lumen 718b is axially compressed in bending, as explained further elsewhere herein.

In the embodiment shown, the stop 748b also includes a plurality of recesses 747b around its perimeter, which may facilitate embedding or otherwise securing the stop 748b across the steering element lumen 718b. For example, during fabrication, the stop 748b may be placed adjacent the steering element lumen 718b and jacket material may be applied around the stop 748b and heated or otherwise caused to flow into the recesses 747b to secure the stop 748b in place. Optionally, the distal end 746b of the coil 746 may be coupled to the stop 748b, e.g., by one or more of bonding with adhesive, welding, fusing, heat welding, and the like. Otherwise, the length of the coil 746 may be set such that the distal end 746b contacts or is spaced away from the distal stop 748b when the tubular body 710 is a desired orientation, e.g., substantially straight.

Similarly, a proximal stop 748a may be provided, e.g., within the handle 730, as shown in FIG. 12, or alternatively, within a proximal portion 720 of the tubular body 710 (not shown). The proximal end 746a of the coil 746 may be separate from the proximal stop 748a, e.g., such that the proximal end 746a contacts or is spaced away from the proximal stop 748a, or the proximal end 746a may be coupled to the proximal stop 748a, as desired.

Although the compression-resistant element 746 is shown extending entirely from the handle 740, through the proximal and intermediate portions 720, 722 of the tubular body 710 (terminating before the distal portion 724), it will be appreciated that the compression-resistant element 746 may have different lengths and/or configurations, e.g., extending proximally only partially from the intermediate portion 722 towards the proximal portion 720, e.g., if the proximal portion 720 is constructed to be resistant to bending. In addition or alternatively, multiple compression-resistant elements may be provided at different locations along the length of the tubular body 710 to provide desired bending characteristics.

Figure 16:
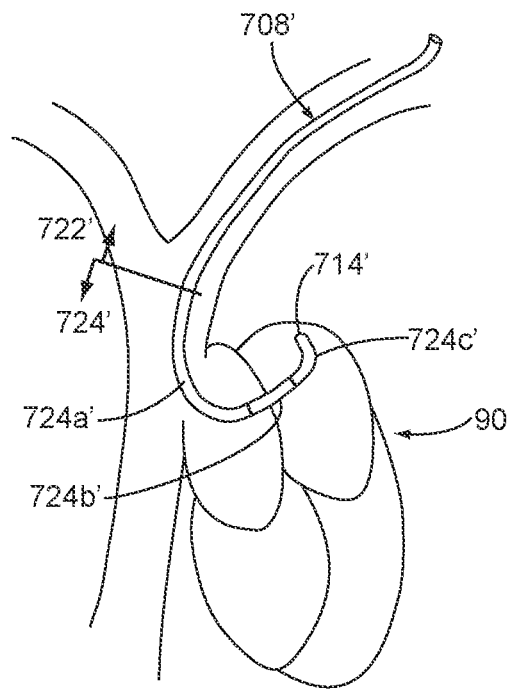
FIG. 16 is a cross-sectional view of a patient's body showing an alternative embodiment of a steerable catheter being used to access chambers of the patient's heart.

For example, as shown in FIG. 16, a catheter 708' is shown that includes a distal portion 724' that includes unsupported and supported regions. In the embodiment shown, the intermediate portion 722' may include a compression-resistant element (not shown), similar to the catheter 708 of FIG. 12, e.g., extending from a proximal portion (not shown) through the intermediate portion 722,' while a steering element (also not shown) extends from the proximal end through to the distal end 714.' The distal portion 724' includes a first portion 724a' that does not include a compression-resistant element, a second portion 724b' distal to the first portion 724a' that includes a compression-resistant element (not shown), and a third portion 724c' distal to the second portion 724b' that does not include a compression-resistant element. Thus, in this configuration, bending forces from the steering element will cause the first and third portions 724a,' 724c' to bend or deflect, while the compression-resistant elements will prevent such forces from being transferred to the second portion 724b' of the distal portion 724' as well as the intermediate portion 722,' thereby minimizing bending forces on those portions.

Returning to FIGS. 12 and 13, similar to other embodiments herein, the catheter 708 may include an inner liner 740, e.g., at least partially or entirely surrounding or otherwise defining the central lumen 718a and/or including one or more coatings, a reinforcement layer 742 surrounding the inner liner 740, and an outer jacket 744 surrounding and/or encasing the reinforcement layer 742, e.g., as identified in FIG. 13A. The reinforcement layer 742 and/or outer jacket 744 may be attached to the inner liner 740, e.g., by laminating, adhering, adhesive bonding, ultrasonic welding, reflowing or other heating, and the like, as described elsewhere herein. Optionally, an inner liner (not shown) may also at least partially surround the steering element lumen 718b, which may be formed from a lubricious material and/or may include one or more coatings on its inner surface, similar to the inner liner 740.

Optionally, any or all of the inner liner 740, reinforcement layer 742, and/or outer jacket 744 may be formed from multiple layers of like or different materials (not shown), e.g., to provide desired material properties in the different portions of the catheter 708. In exemplary embodiments, the outer jacket 744 may be formed from PEBA's, nylons, urethanes, and/or other thermoplastic material, e.g., such that the material of the outer jacket 744 may be heated and reflowed and/or otherwise formed around the components defining the lumens 718, e.g., as described elsewhere herein.

In one embodiment, one or more of the layers of the tubular body 710 may have a substantially homogenous construction between the proximal and distal ends 712, 714. Alternatively, the construction may vary along the length of the tubular body 710 to provide desired properties, e.g., between the proximal, intermediate, and distal portions 720, 722, 724. For example, the proximal portion 720 adjacent the proximal end 712 may be substantially rigid or semi-rigid, e.g., providing sufficient column strength to allow the distal end 714 of the tubular body 710 to be pushed or otherwise manipulated from the proximal end 712, while the distal portion 724 may be substantially flexible.

With particular reference to FIGS. 13A-13D, the reinforcement layer 742 may include one or more reinforcing members, e.g., wound in a braided or other helical configuration around the inner liner 740, e.g., using a braiding apparatus such as that shown in FIGS. 4A and 4B, and the outer jacket 744 may include one or more tubular layers surrounding the reinforcement layer 742 and/or between the reinforcement layer 742 and the inner liner 740. In an exemplary embodiment, the reinforcement layer 742 may include a plurality of, round or flat wires, filaments, strands, or other reinforcement members, e.g., formed from metal, such as stainless steel, plastic, such as PEEK, glass, woven or twisted fibers, such as aramid, and the like, or composite materials.

In addition, the location of the reinforcement layer 742 may vary relative to the central lumen 718a and/or steering element 718b. For example, FIGS. 13A-13D show that the steering element lumen 718b may be braided into the reinforcement layer 742 along the proximal, intermediate, and distal portions 720-724 of the tubular body 710. Optionally, at one or more regions, the steering element lumen 718b may transition outside the reinforcement layer 742. For example, at the proximal end 712 of the tubular body, the steering element lumen 718b may transition outside the reinforcement layer 742 (not shown), to facilitate accessing the steering element lumen 718b, e.g., to insert and/or otherwise couple the steering element 746 to the actuator 734, similar to other embodiments herein.

The tubular body 710 may be fabricated using similar methods and materials as other embodiments described herein. For example, using a braiding apparatus similar to that shown in FIGS. 4A and 4B, a primary mandrel 2a and liner material 4a may be fed along the braiding apparatus configured to define the central lumen 718a (after the mandrel 4a is removed) and elements 6 may be braided around the primary mandrel 4a to provide the reinforcement layer 742. Simultaneously, a secondary mandrel 2b may be fed adjacent the primary mandrel 2a, e.g., optionally, with a secondary liner (not shown) configured to define the steering element lumen 718b. With the secondary mandrel 2b in the A1 position shown in FIG. 4B, the elements 6 of the reinforcement layer 742 may pass over and under the secondary mandrel 2b, thereby braiding the secondary mandrel 2B (and the resulting steering element lumen 718b) into the reinforcement layer 742. Jacket material 7 may be applied around the wrapped assembly, e.g., to provide one or multiple tubular bodies 8, similar to other embodiments herein.

During assembly of an individual catheter, a length of the tubular body material 8 may be provided and, after removing the secondary mandrel in the steering element lumen 718b, the compression-resistant element 746 may be inserted into the lumen 718b and positioned at the desired location. A steering element may also be inserted into the lumen 718b, e.g., through the compression-resistant element 746. Additional components, e.g., the handle 730, stops 748, one or more tip segments (not shown) may then be added to the assembly, as desired to provide a finished catheter 708, e.g., similar to that shown in FIG. 12. Optionally, other components, e.g., one or more sensing elements, electrodes, and the like, may be added to the catheter as desired, similar to other embodiments herein.

Alternatively, the compression-resistant element 746 may be introduced into the tubular body during the braiding process. For example, a coil may be created, e.g., using the spinning action of a horn gear (e.g., one of horn gears 72) and/or driving a coiling apparatus positioned through or along the central axis of one of the horn gears, a tightly-wound coil may be formed and fed around the secondary mandrel 2b or may be used instead of the secondary mandrel 2b. In another alternative, a formed coil may be fed around the secondary mandrel 2b (or instead of the secondary mandrel 2b). Optionally, a coil pulled into the assembly may include a permanent or temporary tensile element to avoid expansion of the coil during assembly. In any of these alternatives, liner material may be wrapped directly around the coil material or a spacer or shim may be provided around or adjacent the coil material, e.g., similar to other embodiments herein.

In yet another alternative, material for the steering element may also be fed into the assembly, e.g., within the coil material such that the steering element and compression-resistant element components may be fed substantially continuously along with the other components of the tubular body. Optionally, one or more friction reducing elements may also be fed or applied during assembly, e.g., one or more liners, coatings, and the like (not shown), applied to reduce friction between the steering element and the compression-resistant element and/or between the compression-resistant element and the inner wall of the steering element lumen.

Optionally, it will be appreciated that additional mandrels and/or components may be fed simultaneously using the braiding apparatus. For example, it may be desired to include multiple steering element lumens, e.g., spaced apart from one another around the periphery of the tubular body. In addition or alternatively, it may be desired to include one or more additional auxiliary lumens and/or primary lumens.

Including a compression-resistant element around one or more regions of steering element may provide various advantages. For example, using a compression-resistant element, an actuation or steering wire may be located as far away from the central axis of the catheter (e.g., to the periphery of the catheter shaft), thus minimizing the pull force required to deflect a catheter of the same stiffness and profile (because, while the steering element lumen is reinforced by the braid, it is still located substantially outside the primary braid circle). In addition, the embedded braid may allow for semi-automated incorporation of the steering element actuation lumen(s) into the cross-section of the catheter, as well as providing easy access along the length for various purposes (e.g., bonding of push/pull wire, distal fixation of the flexible compression element, access in the handle to bring the steering element to the handle actuator, etc.).

Figure 15:
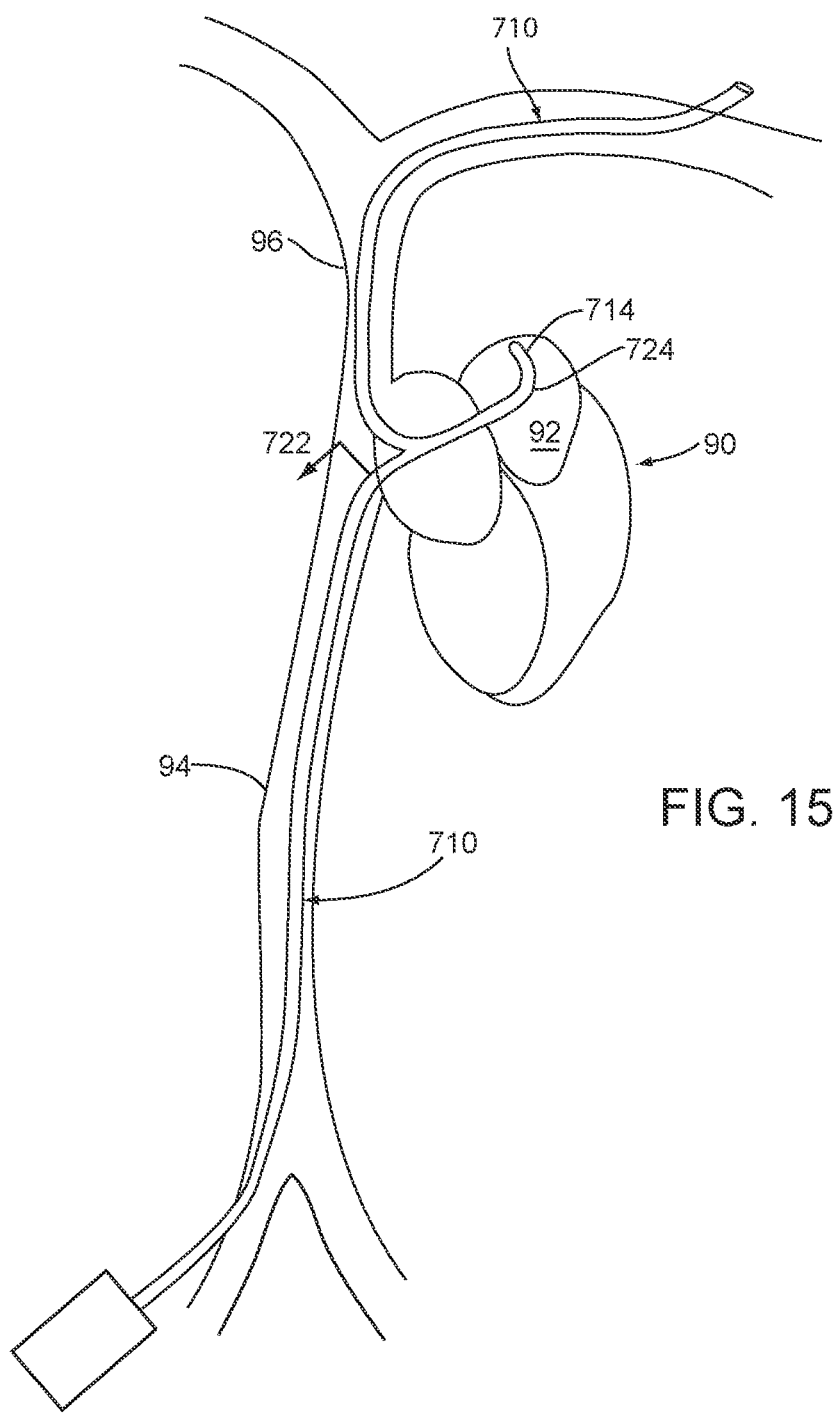
FIG. 15 is a cross-sectional view of a patient's body showing exemplary methods for using a steerable catheter, such as that shown in FIG. 12, to access chambers of the patient's heart.

This design may also enable incorporation of very soft/flexible segment(s) into the catheter at any location along the length of the tubular body without compromising deflection or inducing undesired side deflection. This may be useful both for the ability to atraumatically access and track vessels as well as provide torque transmission through tight bends. In addition, the compression-resistant element may provide the ability to separate deflections forces from the main shaft allowing smooth torqueability without "whip" or changes in degree of deflection, e.g., without significant length changes to the shaft, which may otherwise confound position and other actuators. For example, as shown in FIG. 15, different approaches into chambers 92 of a patient's heart 90 may involve moderate to low tortuosity regions, e.g., along the inferior vena cava 94, and significant tortuosity, e.g., from the superior vena cava 96 and/or otherwise between chambers 92 of the heart 90. The compression-resistant element may facilitate such approaches and focus deflection at the unsupported the distal portion 724.

Further, the compression-resistant element may be free-floating within a supporting lumen to allow it to equilibrate forces at all points. In some cases where necessary it may include a reservoir where "saved" compression element length may be taken or added as need to accommodate large path length changes.

Figure 17:
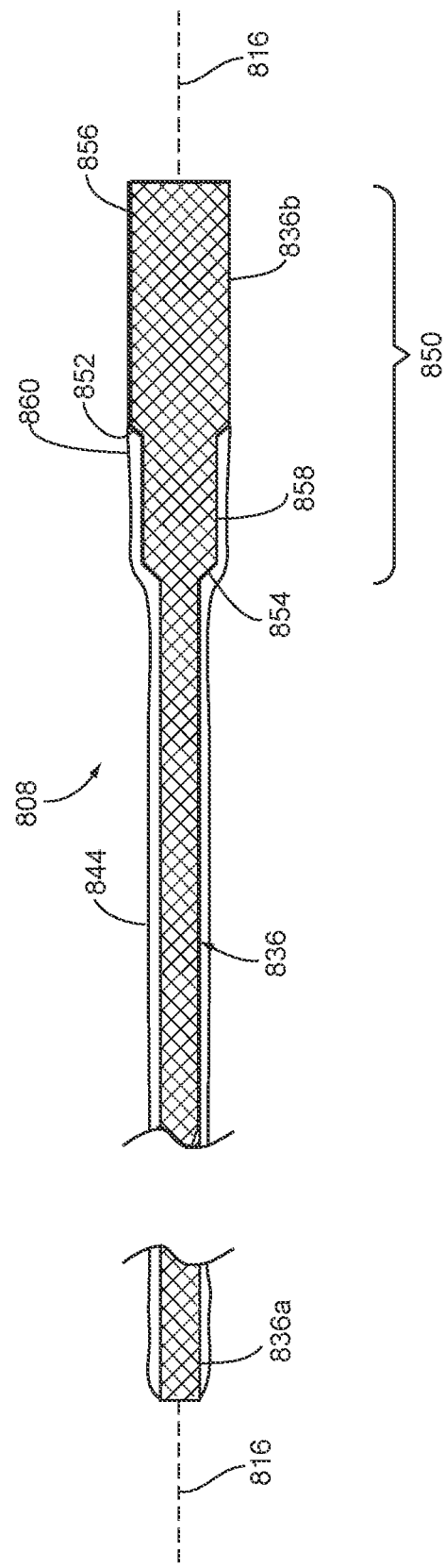
FIG. 17 is a cross-sectional detail of an alternative embodiment of a pull wire construction that may be included in a steerable catheter.

Turning to FIG. 17, another embodiment of steerable catheter 808 is shown that includes a pull wire or steering element 836 that may provide an enlarged distal portion 840 for the catheter 808. For example, in some applications, it may be desired to carry and/or deliver relatively large implants, e.g., valves, stents, grafts, or other tubular prostheses, or devices, e.g., pumps, and the like.

Generally, the steering element 836 includes a proximal end 836a, which may be coupled to an actuator, e.g., on a handle (not shown), and a distal end 836b defining a distal portion 850 sized for introduction into a patient's body. As shown, the distal portion 850 includes one or more tapered regions, e.g., a distal tapered region 852 and a proximal tapered region 854 spaced apart from one another that provide a transition from a distal tip region 856 down to a substantially uniform diameter that extends proximally, e.g., optionally to the proximal end 836a. For example, as shown, the distal tip region 856 may have a substantially uniform diameter cylindrical shape, which, optionally, may include a rounded, tapered, or other substantially atraumatic shape (not shown), e.g., to facilitate advancement of the catheter 808 within a patient's body (not shown).

The distal tapered region 852 transitions from the diameter of the distal tip region 856 to an intermediate region 858 between the tapered regions 852, 854. As shown, the distal tapered region 852 may have a substantially uniform taper around the periphery of the steering element 836 to the diameter of the intermediate region 858. Alternatively, a blunt transition (not shown) may be provided from the distal tip region 856 to the intermediate region 858.

A pull wire ring 860 may be provided on the intermediate region 858, e.g., having an outer diameter similar to the distal tip region 856 and an inner diameter similar to the intermediate region 858, e.g., such that the pull wire ring 860 may be secured around the intermediate region and result in a substantially smooth transition from the pull wire ring 860 to the distal tip region 856. Alternatively, an annular recess may be provided between the distal tip region 856 and a tapered ramp (not shown) sized to receive the pull wire ring 860 such that the tapered ramp provides a transition from the distal tip region 856 to the intermediate region 858.

The proximal tapered region 854 may provide a transition from the intermediate region 856 to the smaller profile of the steering element 836. In particular, the proximal tapered region 854 may have an asymmetrical profile, e.g., such that the step down on the outer side (i.e., closer to the outer periphery of the catheter 808) is smaller than the step down on the inner side (i.e., closer to the central axis 816 of the catheter 808. In this manner, the pull wire ring 860 and steering element 836 may be offset by a maximum distance from the central axis 816, thereby increasing the preference for bending or other deflection distal to the proximal tapered region 854. Alternatively, the proximal tapered region 856 may have a substantially uniform taper, which may still position the steering element 836 away from the central axis 816 of the catheter 808. Optionally, two or more steering elements (not shown) may be provided that are spaced apart from one another around the periphery of the catheter 808, with each steering element having a tapered shape, as described above.

As shown, jacket material 844 may be applied around the steering element 836, e.g., such that the steering element 836 is slidably disposed within a steering element lumen (not shown), similar to other embodiments herein. Optionally, one or more additional lumens (not shown) may be provided adjacent the steering element 836 (and steering element lumen), such as a primary lumen (not shown) disposed around the central axis 816, similar to other embodiments herein. For example, a braiding apparatus, e.g., similar to that shown in FIGS. 4A and 4B may be used to apply a reinforcement layer (not shown) within the jacket material 844, e.g., around a primary lumen and/or at least partially around the steering element 836, e.g., such that the steering element 836 (and lumen) are braided into the reinforcement layer. Alternatively, the reinforcement layer may be applied at other locations, e.g., around the steering element 836 or such that the steering element 836 is outside the reinforcement layer, e.g., at desired locations along the length of the catheter 808.

In addition or alternatively, the catheter 808 may include additional features similar to other embodiments herein, e.g., to provide preferential deflection at the distal portion 850, including one or more compression-resistant elements (not shown) that terminate proximal to the distal portion 850, relatively softer jacket materials at the distal portion 850, and/or different braid densities, as described elsewhere herein.

In accordance with another embodiment, a braiding apparatus may be used to manufacture one or more tubular bodies with reinforcement elements having different pitch angles and/or densities around the circumference and/or along the length of the tubular bodies. For example, using the methods described herein, a tubular shaft may be constructed with an integral/single braid assembly with disparate pitch angle pairs (two or more parallel elements from the same/single braid assembly with different pitch angles), e.g., for the purpose of having both flexibility/kink resistant elements and compression/extension resistant elements in parallel with optionally one or more lumens all in a readily manufacturable process. Moreover, the elements may be made to impart/retain desirable torque and/or other properties to the resulting tubular bodies.

Figure 18:
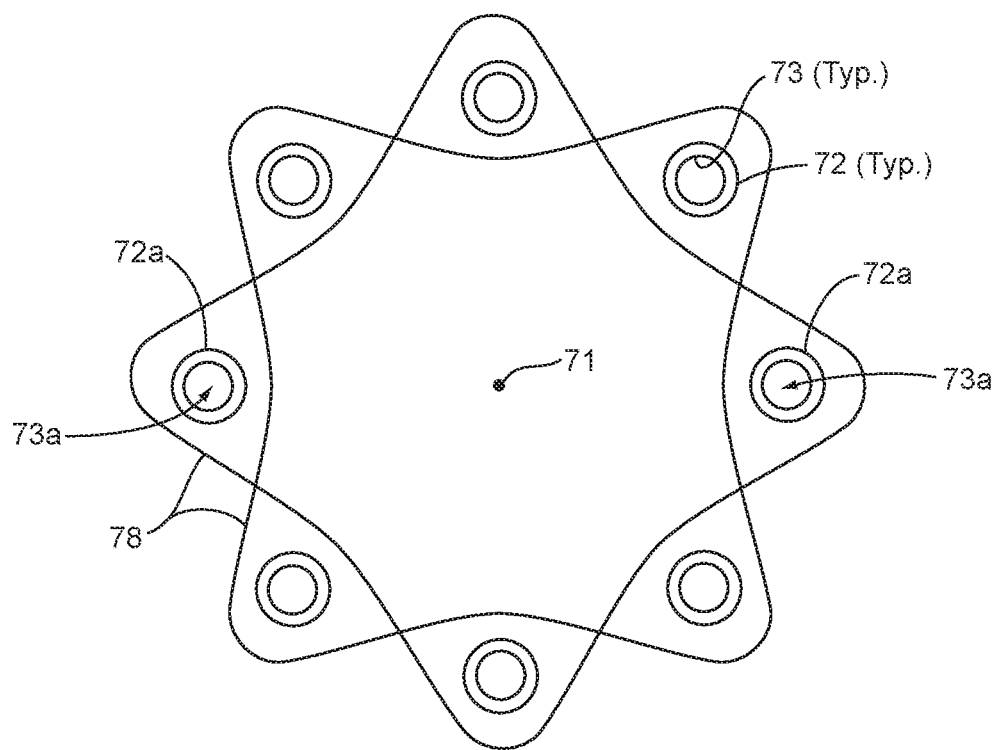
FIG. 18 is a schematic showing an arrangement of horn gears for a braiding apparatus including passages through horn gears for receiving mandrels.

For example, FIG. 18 shows an exemplary braiding apparatus including eight horn gears 72, e.g., carrying sixteen reinforcement element carriers (not shown for simplicity). As described elsewhere herein, e.g., with reference to the braiding apparatus of FIGS. 4A and 4B, the horn gears 72 may pass the carriers 74 of reinforcement members around paths 78, e.g., in a clockwise and/or counterclockwise direction, e.g., with at least some of the carriers travelling clockwise and some travelling counterclockwise, e.g., to create a braided pattern. However, rather than directing a primary mandrel along a central axis 71 between the horn gears 72, one or more primary mandrels (not shown) may be fed through a passage 73a of a horn gear 72 and/or through passages 73a of multiple horn gears 72 to create a variety of braiding configurations.

In exemplary embodiments, disparate pitches within a single braid element may be constructed by braiding at least one permanent (like a cable or a filament) or temporary (like a mandrel for purpose of creating a lumen) element in an axially loaded configuration (through the braid horn gears). The "pitch angle" (between wire angle and main axis) of the braid will, of necessity, be larger over the circumference of the axially loaded element. Conversely, the pitch angle of the braid may be relatively small in regions where either 1) the braided axis/regions from the horn gears without any axial elements loaded, or 2) the braided axis/regions from the horn gears with axially loaded elements that are smaller in diameter as compared to the other axially loaded elements. In addition or alternatively, multiple elements may be put through multiple horn gears to create patterns of kink resistant cores and/or compression resistant cores.

For example, mandrel elements placed through the horn gear lumens will prevent the wires that otherwise would cinch together to stay separated. In the areas of braid where either no element or a smaller element is placed through, the braid will cinch down much further. Thus, although the feed rate of the braiding (braider speed relative to puller speed) is the same for each element, they have different pitch angles. This may be used to construct a braided shaft assembly that has lumens encapsulated in kink and torque inducing braid elements (large pitch angle—defined as angle between element and axis of shaft) while also having interior elements that are compression and extension resistant because they have very small pitch angles (i.e., like a beam or cable). Additionally, these elements may be modulated along the length of the catheter to modulate the desired stiffness, as desired. All of these operations may be completed substantially simultaneously in a single braiding operation with the lumens fully separated.

Figure 19A:
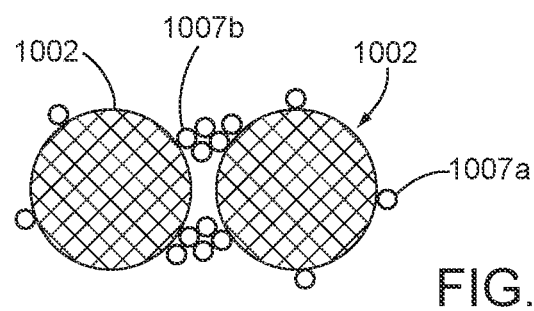
FIG. 19A is a cross-sectional view showing an exemplary braiding configuration of reinforcement elements braided around a pair of primary mandrels that are directed through passages of horn gears, such as in the braiding apparatus of FIG. 18.

Turning to FIG. 19A, an exemplary braiding configuration of reinforcement elements 1007 braided around a pair of primary mandrels or other axial elements 1002 that are directed through passages of horn gears, such as in the braiding apparatus of FIG. 18. In the configuration shown, the mandrels 1002 are fed through passages 73a in opposite horn gears 72a, i.e., located opposite one another across the central axis 71. As with other embodiments herein, optionally liner material (not shown) may be fed around the mandrels 1002, e.g., such that the mandrels 1002 may be subsequently removed (e.g., after applying jacket material, not shown, around the braided mandrels), thereby providing a pair of lumens extending substantially axially along the resulting tubular body.

As a result of this configuration of the mandrels 1002, the reinforcement elements 1007 may have a relatively low density 1007a around the periphery of the mandrels 1007 furthest away from one another, applied by the carriers closest to the horn gears 72a. Conversely, the reinforcement elements may have a relative high density 1007b around the periphery of the mandrels 1002 closest to one another, e.g., applied by the carriers that are further from the horn gears 72a. Alternatively, one or more relatively small mandrels (not shown), i.e., substantially smaller than the mandrels 1002, may be fed through horn gear passages spaced apart from the horn gears 72a, which may result in the small mandrel(s) being braided into the high density region of the reinforcement elements 1007b.

Figure 19B:
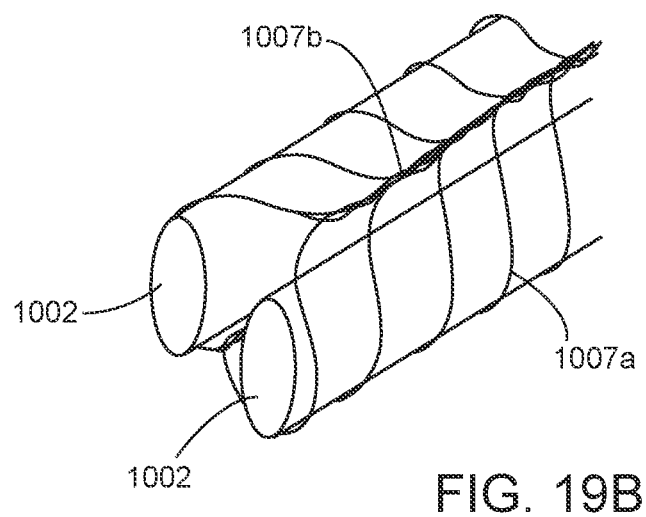
FIGS. 19B and 19C are perspective views of exemplary embodiments of braiding configurations that may be applied around primary mandrels, e.g., to provide substantially uniform spacing or variable spacing, respectively, of the reinforcement elements along the mandrels.
Figure 19C:
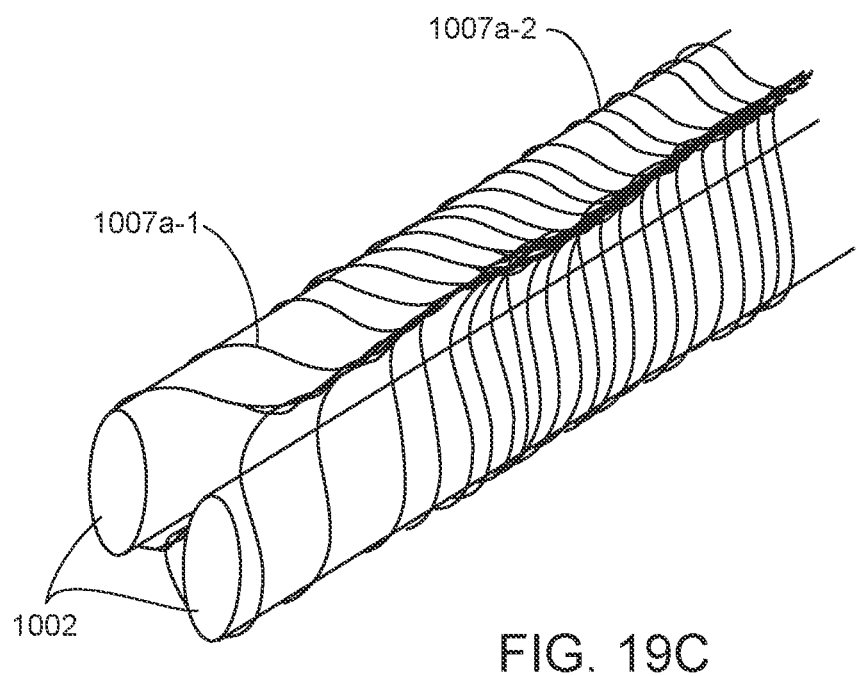

In addition to the distributed density of the reinforcement elements 1007, this configuration may provide varying pitch angles around the peripheries of the mandrels. For example, as shown in FIG. 19B, the low density region of the reinforcement elements 1007a may define relative high pitch angles, e.g., having properties similar to a coil, while the high density region 1007b may define relatively low braid angles, e.g., similar to a braided cable, thereby providing both flexibility/kink resistant properties and compression/extension resistant properties to the resulting tubular body. Optionally, as shown in FIG. 19C, the feed rate and/or pitch of the reinforcement elements 1007 may be varied during operation of the braiding apparatus, e.g., to provide a more compression/extension resistant section where the reinforcement elements 1007a-1 are spaced relatively further apart and a more flexible section where the reinforcement elements 1007a-2 are spaced relatively closer together.

Turning to FIGS. 20A and 20B, another exemplary braiding configuration of reinforcement elements 1017 braided around a single primary mandrel 1012 fed through a passage 73 of a horn gear 72 of a braiding apparatus, such as that shown in FIG. 18. In this embodiment, the reinforcement elements 1017a are less dense from carriers closest to the horn gear 72 through which the mandrel 1012 is fed and the reinforcement elements 1017a are more dense from the carriers further away from the horn gear 72.

Turning to FIG. 21, exemplary braiding configuration of reinforcement elements braided around three primary mandrels 1022, which may be fed through passages of horn gears that are spaced equally apart around the braiding apparatus (not shown). Thus, in this manner, the density of the reinforcement elements 1027a may be lower around the outer peripheries of the mandrels 1022 and may be higher at the region 1027b between the mandrels 1022.

Figure 22A:
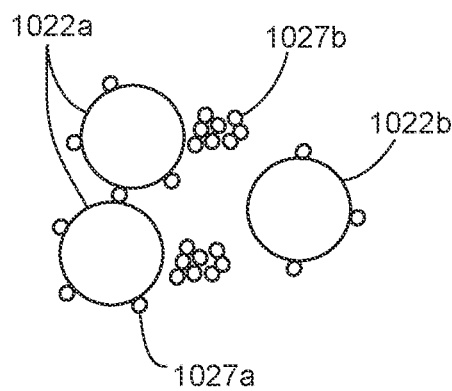
Figure 22B:
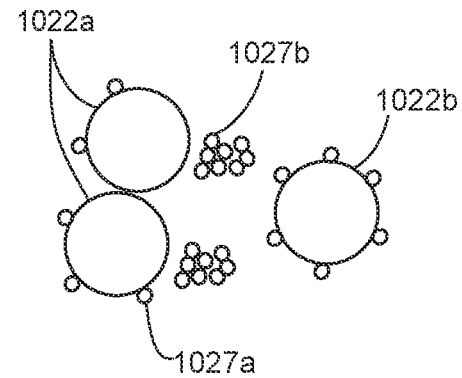

FIGS. 22A and 22B show alternative configurations of braiding patterns around three mandrels 1022 where two of the mandrels 1022a are closer to one another than the third mandrel 1022b. For example, in FIG. 22A, the first mandrels 1022a may be fed through adjacent horn gears (adjacent to one another around the circle of the braiding apparatus) with the second mandrel 1022b fed through a horn gear opposite the adjacent horn gears. Thus, in this alternative, the density of the reinforcement elements 1027a may be lower around the first mandrels 1022 including the area between the first mandrels, while the density of the reinforcement elements 1027b between the first and second mandrels 1022a, 1022b may be higher, as shown. Further, in FIG. 22B, the first mandrels 1022a may be fed through the same horn gear passage, which will result in no reinforcement elements being braided between the first mandrels 1022a as shown. However, the density of the reinforcement elements 1027b between the first and second mandrels 1022a, 1022b may be higher than around the outer peripheries of the mandrels 1022.

As shown in the embodiments of FIGS. 19A-22B, the mandrels 1002-1022 may be fed through the horn gears and reinforcement elements 1007-1027 may be braided around them without any other mandrels or supports. As the reinforcement elements are braided around the mandrel(s), they may cause the mandrel(s) to automatically center and/or stay in a substantially constant radial position, e.g., relative to the central axis 71 of the braiding apparatus. Optionally, a relatively small cable or other elongate element (not shown) may be fed along the central axis 71 such that the mandrels are positioned adjacent this central element, e.g., symmetrically or asymmetrically around the central element, as the reinforcement elements are braided around the mandrels, e.g., to stabilize the components and/or ensure they remain in the desired orientation. This central element may remain within the resulting tubular body (i.e., after applying the outer jacket) or may be removed, as desired.

Figure 23:
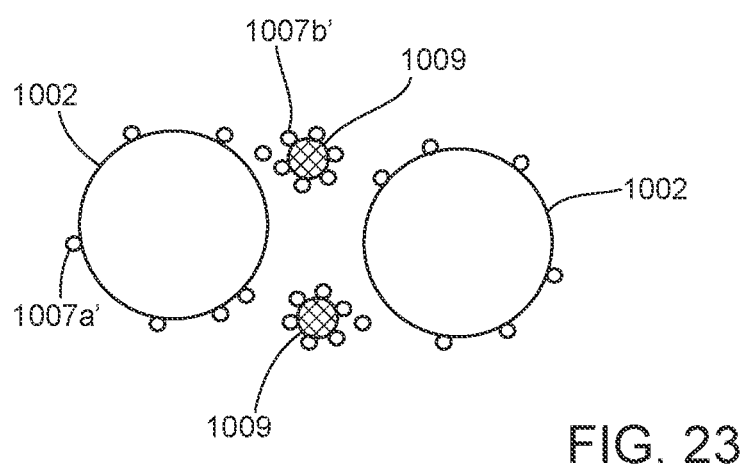
FIG. 23 is a cross-sectional view showing an exemplary braiding configuration of reinforcement elements braided around two primary mandrels spaced apart from relatively small secondary mandrels.

In addition or alternatively, one or more cables or other relatively small elongate elements may be fed from other horn gears, i.e., other than the horn gears through which the primary mandrel(s) are fed. For example, FIG. 23 shows an exemplary embodiment of an exemplary braiding configuration of reinforcement elements 1007 braided around two primary mandrels 1002 spaced apart from relatively small secondary mandrels 1009. Similar to the configuration shown in FIG. 19A, the mandrels 1002 may be fed through passages 73a in opposite horn gears 72a, e.g., as shown in FIG. 18. In addition, secondary mandrels 1009 may be fed through passages of horn gears halfway between the horn gears 73a, i.e., opposite one another (or alternatively at other positions), such that the secondary mandrels 1009 are braided into the more dense regions 1007b' of the reinforcement elements. These secondary elements 1009 may remain in the resulting tubular body or may be removed, as desired.

Although several exemplary embodiments and configurations have been described, it will be appreciated that many other different configurations are possible within a standard single braiding head, e.g., including multiple profiles of wire or polymers; different ranges in sizes of the mandrels; different ranges in ability to distribute the reinforcement elements (ways of ensuring only certain wires/polymers are used for the high pitch angle elements, and vice-versa); different ranges of mandrel or permanent elements both in size, shape, and material (round, flat, angular, I beam, elastomeric, large, small, etc.); different ranges of jacket materials and configurations, which may impart additional stiffness or flexibility as needed; different numbers of horn gear lumens used, and the like. All these variations may provide benefits that can be appreciated by those skilled in the arts for any given catheter challenge where an enabling feature is the ability to have a highly manufacturable catheter with integral elements individually optimized.

With reference to the previous embodiments, it will be appreciated that lumens and/or mandrels used to create them as described may be replaced by wires, conductors, optical fibers, axial reinforcing elements, e.g., aramid fibers, UHMWPE, or other axial elements. in order to incorporate such elements into the catheter construction for the purpose achieving desired mechanical or functional performance.

In addition, it will be appreciated that the lumens formed by the mandrels used in the methods described herein may not extend along the entire length of the resulting tubular bodies. For example, as described above, a mandrel may be positioned such it is braided into the reinforcement members along a first portion and then the mandrel may be repositioned to remove it entirely outside the area of the reinforcement members and jacket material. For example, in the embodiment shown in FIG. 13, the steering element lumen 718a may extend from the distal end 714 of the tubular body 710 towards the proximal end 712, but exit before reaching the proximal end 712, e.g., at a side opening 713.

For example, during manufacturing, a mandrel for the steering element lumen 718b may be braided into the reinforcement layer 742 from the distal end 724 to the location of the side opening 713, whereupon the mandrel may be repositioned outside the braid circle of the braiding apparatus such that the mandrel is not braided or encased in jacket material. Once the tubular device is created, the mandrel may be removed to provide the steering element lumen 718b and side opening 713.

In other applications, one or more lumens may be formed that extend only partially along the length of a tubular member, e.g., from one end to an intermediate location or between two intermediate locations spaced from both ends. Such lumens may be braided into the reinforcement layer along at least a portion of their lengths and/or may be positioned at different locations relative to the reinforcement layer and/or outer jacket, e.g., using the methods described herein. Such lumens extending along a partial length of a tubular device may be useful for constructing balloon catheters (e.g., for easily creating balloon inflation lumens with entry and exit points along the length of the tubular device), electrode carrying catheters (e.g., for easily creating wire carrying lumens with similar entry and exit points), guidewire carrying catheters (e.g., comprising a lumen sized to fit a guide wire, originating at or near the tip of and terminating proximally through the side wall of the tubular device), and/or other devices comprising one or more lumens extending partially along the length of a tubular member.

The foregoing disclosure of the exemplary embodiments has been presented for purposes of illustration and description. It is not intended to be exhaustive or to limit the invention to the precise forms disclosed. Many variations and modifications of the embodiments described herein will be apparent to one of ordinary skill in the art in light of the above disclosure.

Further, in describing representative embodiments, the specification may have presented the method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. An apparatus for performing a procedure within a patient's body, comprising:
   a tubular member comprising a proximal end, a distal end sized for introduction into a patient's body, a central axis extending therebetween, and a distal portion extending distally from an intermediate portion to the distal end;
   a primary lumen extending between the proximal and distal ends and surrounding at least a portion of the central axis;
   a steering element lumen extending at least partially between the proximal and distal ends adjacent the primary lumen;
   a steering element slidably disposed within the steering element lumen and comprising a distal end fixed to the tubular member distal end and a proximal end adjacent the proximal end of the tubular member;
   an actuator on the proximal end coupled to the steering element proximal end such that, actuation of the actuator applies axial tension or compression to the steering element, thereby causing the distal portion to bend;
   a compression-resistant element slidably disposed within the steering element lumen and extending from the proximal end through the intermediate portion adjacent the steering element for preventing forces from the steering element from transferring to the tubular member proximal to the distal portion; and
   a stop within the tubular member intermediate portion adjacent the distal end of the compression-resistant element for limiting compression of the tubular member in bending when the distal end of the compression-resistant element contacts the stop,
wherein the compression-resistant element includes a distal end loose within the intermediate portion, thereby defining the distal portion between the compression-resistant element distal end and the tubular member distal end.

2. The apparatus of claim 1, wherein the compression-resistant element comprises a coil surrounding the steering element between the proximal end and the intermediate portion.

3. The apparatus of claim 2, wherein the coil comprises one of a tightly wound coil, a counter-wound coil tube, a coil tube with an attached tensile element, and a laser cut tube.

4. The apparatus of claim 1, wherein the tubular member comprises:
one or more reinforcement members comprising windings extending around the primary lumen between the proximal and distal ends; and
one or more layers surrounding the one or more reinforcement members,
wherein the tubular member comprises a first portion in which at least some of the windings pass between the primary lumen and the steering element lumen and at least some of the windings surrounding both the primary lumen and the steering element lumen.

5. The apparatus of claim 4, wherein the tubular member comprises a second portion in which either a) all of the windings surround both the primary lumen and the steering element lumen or b) all of the windings surround the primary lumen and the steering element lumen is disposed outside the windings.

6. The apparatus of claim 4, wherein the first portion includes the intermediate portion of the tubular member.

7. The apparatus of claim 6, wherein the first portion includes the distal portion of the tubular member.

8. The apparatus of claim 4, wherein the tubular member comprises a second portion adjacent the proximal portion wherein all of the windings surround the primary lumen and the steering element lumen is disposed outside the windings.

9. The apparatus of claim 1, wherein the central lumen is defined by a liner comprising an inner surface substantially surrounding the central lumen.

10. The apparatus of claim 9, wherein the liner comprises a lubricious coating on the inner surface.

11. The apparatus of claim 1, wherein the steering element lumen is defined by a liner comprising an inner surface substantially surrounding the steering element lumen.

12. The apparatus of claim 1, wherein the steering element lumen is smaller than the primary lumen.

13. The apparatus of claim 1, wherein the primary lumen communicates with an outlet in the distal end.

14. The apparatus of claim 1, wherein the tubular member comprises:
one or more reinforcement members comprising windings extending around the primary lumen between the proximal and distal ends; and
one or more layers surrounding the one or more reinforcement members,
wherein the steering element lumen is braided into the reinforcement layer along the distal portion.

15. The apparatus of claim 14, wherein the stop is located at a transition from the intermediate portion to the distal portion.

16. The apparatus of claim 1, wherein the stop is embedded into material of the tubular member.

17. The apparatus of claim 1, wherein the stop is fixed within or across the steering element lumen and the steering element is slidably disposed through the stop.

18. The apparatus of claim 1, wherein the stop is sized to abut the compression-resistant element distal end with the steering element slidably disposed through the stop.

19. An apparatus for performing a procedure within a patient's body, comprising:
a tubular member comprising a proximal end, a distal end sized for introduction into a patient's body, a central axis extending therebetween, and a distal portion extending distally from an intermediate portion to the distal end;
a primary lumen extending between the proximal and distal ends and surrounding at least a portion of the central axis;
a steering element lumen extending at least partially between the proximal and distal ends adjacent the primary lumen;
a steering element slidably disposed within the steering element lumen and comprising a distal end fixed to the tubular member distal end and a proximal end adjacent the proximal end of the tubular member;
an actuator on the proximal end coupled to the steering element proximal end such that, actuation of the actuator applies axial tension or compression to the steering element, thereby causing the distal portion to bend;
a compression-resistant element slidably disposed within the steering element lumen and extending from the proximal end through the intermediate portion adjacent the steering element for preventing forces from the steering element from transferring to the tubular member proximal to the distal portion;
a handle coupled to the tubular member proximal end; and
a stop fixed within the handle and disposed adjacent a proximal end of the compression-resistant element for limiting compression of the tubular member in bending when the distal end of the compression-resistant element contacts the stop.

20. The apparatus of claim 19, wherein the compression-resistant element includes a distal end fixed to the tubular member within the intermediate portion, thereby defining the distal portion between the compression-resistant element distal end and the tubular member distal end.

21. The apparatus of claim 19, wherein the compression-resistant element includes a distal end fixed to the tubular member within the intermediate portion such that forces from the steering element are transferred to the distal portion, thereby causing the distal portion to deflect when axial forces are applied to the steering element.

* * * * *